(12) United States Patent
Ito et al.

(10) Patent No.: US 11,453,678 B2
(45) Date of Patent: Sep. 27, 2022

(54) SOLVENT-FREE CROSS-COUPLING REACTION, AND PRODUCTION METHOD USING SAID REACTION

(71) Applicant: NATIONAL UNIVERSITY CORPORATION HOKKAIDO UNIVERSITY, Hokkaido (JP)

(72) Inventors: Hajime Ito, Hokkaido (JP); Koji Kubota, Hokkaido (JP)

(73) Assignee: NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 0 days.

(21) Appl. No.: 17/287,423

(22) PCT Filed: Oct. 23, 2019

(86) PCT No.: PCT/JP2019/041566
§ 371 (c)(1),
(2) Date: Apr. 21, 2021

(87) PCT Pub. No.: WO2020/085396
PCT Pub. Date: Apr. 30, 2020

(65) Prior Publication Data
US 2021/0387994 A1    Dec. 16, 2021

(30) Foreign Application Priority Data
Oct. 23, 2018  (JP) .............................. JP2018-198915

(51) Int. Cl.
| | | |
|---|---|---|
| C07D 487/22 | (2006.01) | |
| B01J 23/44 | (2006.01) | |
| C07C 17/275 | (2006.01) | |
| C07C 41/22 | (2006.01) | |
| C07C 45/68 | (2006.01) | |
| C07C 67/343 | (2006.01) | |
| C07C 209/10 | (2006.01) | |
| C07D 209/88 | (2006.01) | |
| C07D 333/28 | (2006.01) | |
| C07D 333/36 | (2006.01) | |
| C07F 5/02 | (2006.01) | |

(52) U.S. Cl.
CPC ............ *C07D 487/22* (2013.01); *B01J 23/44* (2013.01); *C07C 17/275* (2013.01); *C07C 41/22* (2013.01); *C07C 45/68* (2013.01); *C07C 67/343* (2013.01); *C07C 209/10* (2013.01); *C07D 209/88* (2013.01); *C07D 333/28* (2013.01); *C07D 333/36* (2013.01); *C07F 5/025* (2013.01); *C07C 2603/20* (2017.05); *C07C 2603/24* (2017.05); *C07C 2603/50* (2017.05)

(58) Field of Classification Search
CPC .................................................. C07D 487/22
See application file for complete search history.

(56) References Cited

U.S. PATENT DOCUMENTS 10,793,504 B2 * 10/2020 Pinchman ............ C07D 263/56

OTHER PUBLICATIONS

Office Action for corresponding Japanese Application No. 2020-553437 dated Jul. 13, 2021 and its English Translation.
Jiang, Zhi-Jiang et al., "Liquid-Assisted Grinding Accelerating: Suzuki-Miyaura Reaction of Aryl Chlorides under High-Speed Ball-Milling Conditions," Journal of Organic Chemistry, 2016, 81 (20), pp. 10049-10055.
Schneider, Franziska et al., "The Suzuki-Miyaura Reaction under Mechanochemical Conditions," Organic Process Research & Development, 2009, 13 (1), pp. 44-48.
Shao, Qiao-Ling et al., "Solvent-free mechanochemical Buchwald-Hartwig amination of aryl chlorides without inert gas protection," Tetrahedron Letters, Jun. 6, 2018, 59(23), pp. 2277-2280.
Hernandez, J. G. et al., "Useful chemical activation alternatives in solvent-free organic reactions," Comprehensive Organic Synthesis (2nd Edition), vol. 9, 2014, pp. 287-314.
Stolle, Achim et al., "Solvent-free reactions of alkynes in ball mills: it is definitely more than mixing," Pure and Applied Chemistry, 2011, 83(7), pp. 1343-1349.
Akira Suzuki, Journal of Synthetic Organic Chemistry, Japan, 2005, vol. 63, No. 4, 312.
Ruiz-Castillo, P., Buchwald, S. L. Chem. Rev., 2016, vol. 116, 12564.
Howard, J. L., Cao, Q., Browne, D. L. Chem. Sci. 2018, vol. 9, 3080.
International Preliminary Report on Patentability for corresponding International Application No. PCT/JP2019/041566, dated Feb. 4, 2020 and English translation.
Decision to Grant a Patent for corresponding Japanese Application No. 2020-553437 mailed Jan. 25, 2022 and its English Translation.
First Office Action for corresponding Chinese Application No. 201980069500.1 dated Mar. 8, 2022 and its English Machine Translation.

(Continued)

*Primary Examiner* — Golam M Shameem
(74) *Attorney, Agent, or Firm* — Renner, Otto, Boisselle & Sklar, LLP

(57) ABSTRACT

Disclosed is a cross-coupling reaction method which forms a chemical bond selected from C—N, C—B, C—C, C—O and C—S bonds, the method comprising:
  preparing an aromatic compound (1) having a leaving group;
  preparing a compound (2) capable of undergoing a cross-coupling reaction selected from an aromatic amino compound (2-1), a diboronic acid ester or the like (2-2), an aromatic boronic acid or the like (2-3), an aromatic compound (2-4) having a hydroxyl group and an aromatic compound (2-5) having a thiol group; and
  performing a cross-coupling reaction of the compound (1) with the compound (2) in the presence of a palladium catalyst, a base and a compound (4) having a carbon-carbon double bond or a carbon-carbon triple bond, in the absence of a solvent.

12 Claims, 1 Drawing Sheet

(56) References Cited

OTHER PUBLICATIONS

Chen Xin-bing, "Latest advances in the industrial application of Suzuki coupling reaction catalyzed by palladium", Industrial Catalyst, vol. 8 No. 3 May 2000, p. 23-26 and its English Machine Translation.
Extended European Search Report (EESR) in corresponding European Application No. 19876774.1 dated Jun. 15, 2022.
Kubota Koji et al., "Olefin-accelerated solid-state C-N cross-coupling reactions using mechanochemistry", Nature Communications, vol. 10, No. 111, Jan. 10, 2019, p. 1-11.

* cited by examiner

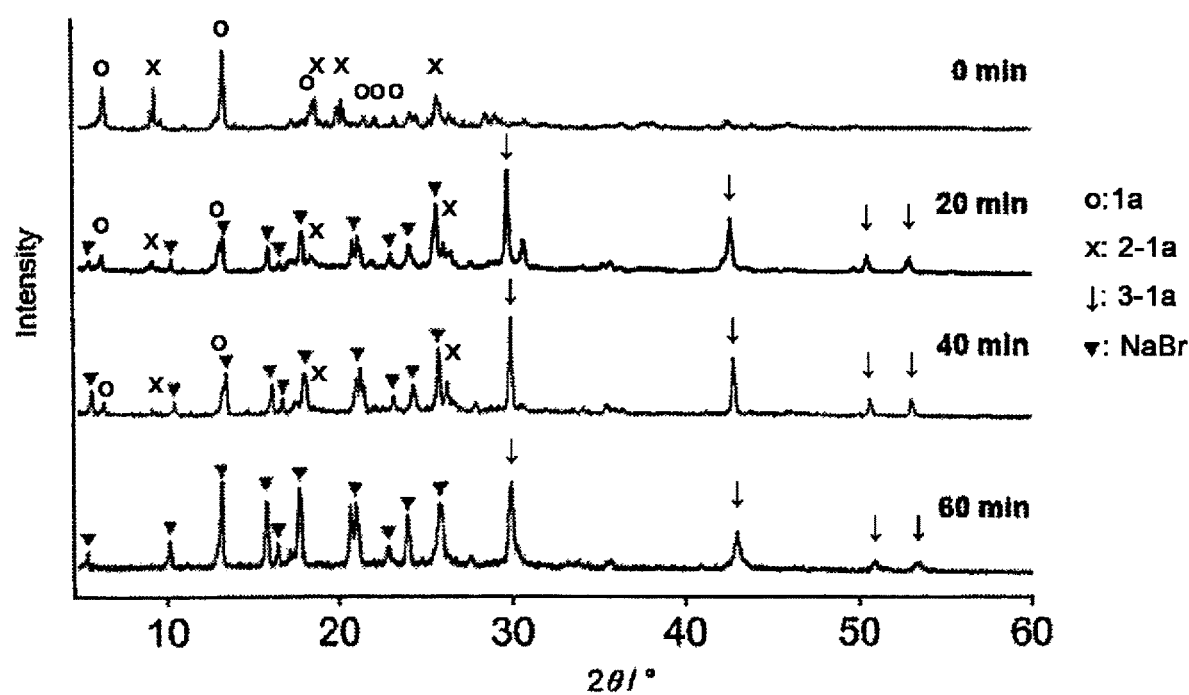

SOLVENT-FREE CROSS-COUPLING REACTION, AND PRODUCTION METHOD USING SAID REACTION

TECHNICAL FIELD

The present invention relates to a novel cross-coupling reaction method without using an organic solvent (solvent-free cross-coupling reaction method), and also relates to a method for producing a cross-coupling reaction product using said method.

BACKGROUND ART

A cross-coupling reaction using a palladium catalyst (palladium-catalyzed cross-coupling reaction) is an essential synthetic reaction for producing various industrial materials such as antihypertensive drugs and liquid crystal materials. Its importance in synthetic chemistry is evident from the fact that Dr. Akira Suzuki, Dr. Eiichi Negishi and Dr. Richard Heck were awarded the 2010 Nobel Prize in Chemistry for "Developing Palladium-Catalyzed Cross-Coupling Reactions" (see NPLs 1 and 2).

CITATION LIST

Non-Patent Literature

[NPL 1] Akira Suzuki, Journal of Synthetic Organic Chemistry, Japan, 2005, Vol. 63, No. 4, 312
[NPL 2] Ruiz-Castillo, P., Buchwald, S. L. Chem. Rev., 2016, Vol. 116, 12564
[NPL 3] Howard, J. L., Cao, Q., Browne, D. L. Chem. Sci. 2018, Vol. 9, 3080.

SUMMARY OF INVENTION

Technical Problem

Generally, the cross-coupling reaction requires a relatively large amount of an organic solvent, and the reactant is dissolved in the organic solvent to cause the cross-coupling reaction.

In recent years, there has been a need to improve the use of the organic solvent since the use of the large amount of the organic solvent is not preferable for the working environment of workers, the use of the large amount of the organic solvent is not preferable for the protection of the global environment, and the disposal of the large amount of the used organic solvent is not easy.

Therefore, there is required a cross-coupling reaction method with less impact on the working environment and the global environment.

Organic synthesis methods in which reaction raw materials are brought into direct contact with each other without using an organic solvent are attracting attention as an environmentally-friendly synthesis method without using an organic solvent, and are interesting from both academic and industrial perspectives.

Although there has been reported a palladium-catalyzed cross-coupling reaction which substantially uses no organic solvent, there are still few examples of such reactions, and few palladium-catalyzed cross-coupling reactions which proceed efficiently for various starting materials (see NPL 3, Scheme 6).

Therefore, it is an object of the present invention to provide a palladium-catalyzed cross-coupling reaction method capable of proceeding efficiently for various starting materials, while reducing an amount of an organic solvent used, preferably without substantially using an organic solvent, preferably under milder reaction conditions in a shorter time, in higher yield. It is also an object of the present invention to provide a cross-coupling reaction in which at least one of starting materials is a solid, and a cross-coupling reaction in which at least two of starting materials are solids.

Means for Solving the Problems

As a result of intensive study, the present inventors thought that when an organic solvent is not used in a palladium-catalyzed cross-coupling reaction, a palladium catalyst is not sufficiently dispersed in reaction raw materials (or a mixture) (diffusion rate-determining) and aggregation of the palladium catalyst leads to deactivation of the catalyst, thus causing hindrance of the reaction progress.

Therefore, the present inventors thought that addition of a small amount of a compound having a carbon-carbon double or triple bond during a cross-coupling reaction without using a solvent enables an improvement in dispersibility of the palladium catalyst and suppression of the aggregation of the palladium catalyst.

As a result of actual studies, it has been found that the addition of a small amount of the compound having a carbon-carbon double or triple bond significantly accelerates a palladium-catalyzed cross-coupling reaction for various starting materials without using a solvent, thus completing the present invention.

Thus, the present invention provides, as one aspect, a novel cross-coupling reaction method, which is a cross-coupling reaction method which forms a chemical bond selected from C—N, C—B, C—C, C—O and C—S bonds, the method comprising:

preparing an aromatic compound (1) having a leaving group;

preparing a compound (2) capable of undergoing a cross-coupling reaction selected from an aromatic amino compound (2-1), a diboronic acid ester or the like (2-2), an aromatic boronic acid or the like (2-3), an aromatic compound (2-4) having a hydroxyl group and an aromatic compound (2-5) having a thiol group; and performing a cross-coupling reaction of the compound (1) with the compound (2) in the presence of a palladium catalyst, a base and a compound (4) having a carbon-carbon double bond or a carbon-carbon triple bond, in the absence of a solvent.

The present invention provides, in another aspect, a method for producing a cross-coupling reaction product using the above cross-coupling reaction method which forms a chemical bond selected from C—N, C—B, C—C, C—O and C—S bonds.

Advantageous Effects of Invention

The cross-coupling reaction method of the embodiment of the present invention is capable of proceeding efficiently to form a chemical bond selected from C—N, C—B, C—C, C—O and C—S bonds, while reducing an amount of an organic solvent used, preferably without substantially using an organic solvent, preferably under milder reaction conditions in a shorter time, in higher yield.

Therefore, by using the cross-coupling reaction method of the embodiment of the present invention, it is possible to efficiently produce a cross-coupling product in which a chemical bond selected from C—N, C—B, C—C, C—O and C—S bonds is formed, while reducing an amount of an organic solvent used, preferably without substantially using an organic solvent, preferably under milder reaction conditions in a shorter time, in higher yield.

BRIEF DESCRIPTION OF THE DRAWINGS

FIG. 1 shows an observation of a solid phase palladium-catalyzed C—N coupling reaction of Example 1 by powder X-ray diffraction.

DESCRIPTION OF EMBODIMENTS

A cross-coupling reaction method of an embodiment of the present invention is a cross-coupling reaction method which is a method for newly forming a chemical bond selected from C—N, C—B, C—C, C—O and C—S bond, the method comprising:

<1> preparing an aromatic compound (1) having a leaving group;

<2> preparing a compound (2) capable of undergoing a cross-coupling reaction selected from an aromatic amino compound (2-1), a diboronic acid ester or the like (2-2) (including an ester and an acid thereof), an aromatic boronic acid or the like (2-3) (including an acid and an ester thereof), an aromatic compound (2-4) having a hydroxyl group and an aromatic compound (2-5) having a thiol group; and <3> performing a cross-coupling reaction of the compound (1) with the compound (2) in the presence of a palladium catalyst, a base and a compound (4) having a carbon-carbon double bond or a carbon-carbon triple bond, in the absence of a solvent.

The cross-coupling reaction method of the embodiment of the present invention comprises:

<1> preparing an aromatic compound (1) having a leaving group.

In the present disclosure, the aromatic compound (1) having a leaving group is not particularly limited as long as it has an aromatic group bonded to the leaving group, and the objective cross-coupling reaction of the present invention can be performed.

In the present disclosure, the leaving group of the aromatic compound (1) having a leaving group is not particularly limited as long as it is a leaving group which is usually used in cross-coupling reactions, and the objective cross-coupling reaction of the present invention can be performed.

The leaving group can be generally selected from chloro, bromo, iodo, a diazonium salt, trifluoromethanesulfonate and carboxylic acid derivatives, and also can be selected from chloro, bromo, iodo, a diazonium salt and trifluoromethanesulfonate.

The aromatic group is not particularly limited as long as it is an aromatic group which is usually used, and the objective cross-coupling reaction of the present invention can be performed. The aromatic group can be generally selected from an optionally substituted aryl group (or an aromatic hydrocarbon group) and an optionally substituted heteroaryl group (or a heteroaromatic group).

Examples of the optionally substituted aryl group (or the aromatic hydrocarbon group) include phenyl group, naphthyl group, anthracenyl group (or anthracene group), phenanthrenyl group (or phenanthrene group), biphenyl group, terphenyl group, pyrenyl group (or pyrene group), perylenyl group (or perylene group), triphenylenyl group (or triphenylene group) and the like.

Examples of the optionally substituted heteroaryl group (or the heteroaromatic group) include:

sulfur-containing heteroaryl groups such as thiophenyl group (thiophene group or thienyl group), thienylenyl group (or thiophenediyl group), benzothienyl group, dibenzothienyl group, phenyldibenzothienylenyl group and dibenzothienylenylphenyl group;

oxygen-containing heteroaryl groups such as furanyl group (or furan group), benzofuranyl group, dibenzofuranyl group, phenyldibenzofuranyl group and dibenzofuranylphenyl group;

nitrogen-containing heteroaryl groups such as pyridyl group (or pyridine group), pyridylenyl group (or pyridinediyl group), pyrimidinyl group (or pyrimidine group), pyrazyl group (or pyrazine group), quinolyl group (or quinoline group), isoquinolyl group (or isoquinoline group), carbazolyl group (or carbazole group), 9-phenylcarbazolyl group, acridinyl group (or acrydine group), quinazolyl group (or quinazoline group), quinoxalyl group (or quinoxaline group), 1,6-naphthyridinyl group, 1,8-naphthyridinyl group and porphyrin group (or porphyrin ring); and heteroaryl groups containing two or more heteroatoms (e.g., nitrogen and sulfur), such as benzothiazolyl group (or benzothiazole group).

There is no particular limitation on the substituent, with which the aryl group and the heteroaryl group can be substituted, as long as the objective cross-coupling reaction of the present invention can be performed.

Examples of the substituent include:

alkyl groups having 1 to 24 carbon atoms, for example, 1 to 18 carbon atoms, for example, 1 to 12 carbon atoms, for example, 1 to 8 carbon atoms (e.g., methyl group, ethyl group, n-propyl group, isopropyl group, n-butyl group, isobutyl group, tert-butyl group, pentyl group, hexyl group, octyl group, etc.), alkoxy groups having 1 to 24 carbon atoms, for example, 1 to 18 carbon atoms, for example, 1 to 12 carbon atoms, for example, 1 to 8 carbon atoms (e.g., methoxy group, ethoxy group, n-propoxy group, isopropoxy group, n-butoxy group, isobutoxy group, tert-butoxy group, pentyloxy group, hexyloxy group, octyloxy group, etc.), cycloalkyl groups having 3 to 24 carbon atoms, for example, 3 to 18 carbon atoms, for example, 3 to 12 carbon atoms, for example, 3 to 8 carbon atoms (e.g., cyclopropyloxy group, cyclobutyloxy group, cyclopentyloxy group, cyclohexyloxy group, etc.), alkenyl groups having 1 to 24 carbon atoms, for example, 1 to 18 carbon atoms, for example, 1 to 12 carbon atoms, for example, 1 to 8 carbon atoms (e.g., ethenyl group, propenyl group, butenyl group, pentenyl group, hexenyl group, octenyl group, etc.), alkynyl groups having 1 to 24 carbon atoms, for example, 1 to 18 carbon atoms, for example, 1 to 12 carbon atoms, for example, 1 to 8 carbon atoms (e.g., ethynyl group, propynyl group, butynyl group, pentynyl group, hexynyl group, octynyl group, etc.), aryl groups having 5 to 24 carbon atoms, for example, 5 to 18 carbon atoms, for example, 5 to 12 carbon atoms, for example, 5 to 8 carbon atoms (e.g., phenyl group, naphthyl group, biphenyl group, etc.), aryloxy groups having 5 to 24 carbon atoms, for example, 5 to 18 carbon atoms, for example, 5 to 12 carbon atoms, for example, 5 to 8 carbon atoms (e.g., phenoxy group, naphthyloxy group, biphenyloxy group, etc.), heteroaryl groups having 4 to 24 carbon atoms, for example, 1 to 18 carbon atoms, for example, 1 to 12 carbon atoms, for example, 1 to 8 carbon atoms (e.g., thiophenyl group, furanyl group, carbazole group, benzothiophenyl group, benzofuranyl group, indolyl group, pyrrolyl group, pyridyl group, etc.), acyl groups having 1 to 24 carbon atoms, for example, 1 to 18 carbon atoms, for example, 1 to 12 carbon atoms, for example, 1 to 8 carbon atoms (e.g., acetyl group, propionyl group, butanoyl group, pentanoyl group, heptanoyl group, a group in which a carbonyl group included in the acyl group is substituted with an ester group or an amide group, etc.), amino groups having 1 to 24 carbon atoms, for example, 1 to 18 carbon atoms, for example, 1 to 12 carbon atoms, for example, 1 to 8 carbon atoms (e.g., diphenylamino group, dimethylamino group, etc.), and fluorine (including partial fluorine substitution and complete fluorine substitution), cyano group and nitro group.

The substituents may be crosslinked to each other, and the entire substituent may form a cyclic structure (an aromatic group). Further, the above-mentioned substituent may be further substituted with the above-mentioned substituent.

The aromatic compound (1) having a leaving group can have a plurality of leaving groups. When the aromatic compound (1) having a leaving group has a plurality of leaving groups, it is clear that valence of the aromatic group corresponds to the number of leaving groups.

The aromatic compound (1) having a leaving group can be more specifically represented, for example, by the following general formula (I):

$$A^1\text{-Xn:} \quad (I)$$

wherein $A^1$ is selected from an optionally substituted aryl group and an optionally substituted heteroaryl group, X is a leaving group, and n is an integer of 1 or more.

In the formula (I), the optionally substituted aryl group and the optionally substituted heteroaryl group for $A^1$ can contain, for example, the above-mentioned optionally substituted aryl group and optionally substituted heteroaryl group.

In the formula (I), the substituent of the optionally substituted aryl group and the optionally substituted heteroaryl group can be, for example, the above-mentioned substituent.

The substituents may be crosslinked to each other, and the entire substituent may form a cyclic structure (an aromatic group). Further, the above-mentioned substituent may be further substituted with the above-mentioned substituent.

In the formula (I), the leaving group for X may be the above-mentioned leaving group, and is preferably selected from chloro, bromo, iodo, a diazonium salt and trifluoromethanesulfonate.

In the formula (I), n is 1 or more, and is not particularly limited as long as a cross-coupling reaction can be performed. n may be, for example, 1 to 8, 1 to 6, and 1 to 4. n can be appropriately selected.

Therefore, for example, in the formula (I), when n=2, $A^1$ is divalent, and when n=4, $A^1$ is tetravalent.

The above-mentioned optionally substituted aryl group and optionally substituted heteroaryl group mainly exemplify names of the monovalent aryl groups and heteroaryl groups. However, it is easy for a person skilled in the art to understand that hydrogen atoms can be removed according to the number of leaving groups and thus an aryl group and a heteroaryl group with appropriate valence can be used, and those polyvalent aryl group and heteroaryl group can be included.

It is possible to more specifically exemplify, as $A^1$ of the aromatic compound (1) having a leaving group, for example, the following groups:

naphthyl groups such as naphthyl group, an aryl (e.g., phenyl, etc.) naphthyl group, a naphthyl group having an alkylene (e.g., ethylene, etc.) crosslink and a naphthyl group having an arylene (e.g., phenylene, etc.) crosslink;

phenanthrenyl groups;

anthracenyl groups such as anthracenyl group, an aryl (e.g., phenyl, etc.) anthracenyl group, a diaryl (e.g., dinaphthyl, etc.) anthracenyl group, a diarylboryl (e.g., bis(trialkylphenyl)boryl, etc.) anthracenyl group;

pyrenyl groups such as pyrenyl group and an alkyl (e.g., t-butyl, etc.) pyrenyl group;

biphenyl groups such as biphenyl group and a biphenyl group having an alkylene (e.g., propyrene, isopropyrene, etc.) crosslink;

terphenyl groups such as terphenyl group and a tetraaryl (e.g., tetraphenyl, etc.) terphenyl group;

triphenylenyl groups;

phenyl groups such as a 2-aryl (e.g., phenyl, etc.) ethenylphenyl group, a 1,2,2-triaryl (e.g., triphenyl, etc.) ethenylphenyl group, a 2-aryl (e.g., phenyl, etc.) ethynylphenyl group, phenyl group, an alkyl (e.g., methyl) phenyl group, a dialkyl (e.g., dimethyl) phenyl group, an alkoxy (e.g., methoxy) phenyl group, a dialkylamino (e.g., dimethylamino) phenyl group, a diaryl (e.g., diphenyl) aminophenyl group, a perfluoroalkyl (e.g., trifluoromethyl) phenyl group, an alkyl (e.g., ethyl) oxycarbonylphenyl group and an alkanoyl (e.g., acyl) phenyl group;

aryl (e.g., phenyl, etc.)-substituted carbazolyl groups;

anthracene-9.10-dione groups, aryl (e.g., phenyl, etc.)-substituted thienyl groups; and divalent or higher polyvalent groups, such as phenylene group, an aryl (e.g., bis(3,5-methylphenyl), etc.) porphyrin ring and a pyrene-tetra-yl group.

It is possible to use, as the aromatic compound (1) having a leaving group, commercially available compounds.

The cross-coupling reaction method of the embodiment of the present invention comprises:

<2> preparing a compound (2) capable of undergoing a cross-coupling reaction selected from an aromatic amino compound (2-1), a diboronic acid ester or the like (including an ester and an acid) (2-2), an aromatic boronic acid or the like (including an acid or an ester thereof) (2-3), an aromatic compound (2-4) having a hydroxyl group, and an aromatic compound (2-5) having a thiol group.

In the present disclosure, the compound (2) capable of undergoing a cross-coupling reaction is not particularly limited as long as it corresponds to compounds (2-1) to (2-5) capable of undergoing a cross-coupling reaction with the above-mentioned aromatic compound (1) having a leaving group, and is selected from an aromatic amino compound (2-1), a diboronic acid ester or the like (2-2), an aromatic boronic acid or the like (2-3), an aromatic compound (2-4) having a hydroxyl group and an aromatic compound (2-5) having a thiol group.

In the present disclosure, the aromatic amino compound (2-1) is not particularly limited as long as it has an amino group bonded to an aromatic group, the amino group having hydrogen, and undergoes a cross-coupling reaction with the above-mentioned aromatic compound (1) having a leaving group to give a cross-coupling product in which an N—C bond is formed.

The aromatic group can be selected, for example, from an optionally substituted aryl group (or an aromatic hydrocarbon group) and an optionally substituted heteroaryl group (or a heteroaromatic group). The aromatic amino compound (2-1) can have up to two aromatic groups. When the aromatic amino compound (2-1) has two aromatic groups, the two aromatic groups may be either crosslinked or bonded to each other.

The aromatic amino compound (2-1) may have two substituents, which may be bonded to each other to entirely form one cyclic structure, for example, an aromatic group.

Examples of the optionally substituted aryl group (or the aromatic hydrocarbon group) include phenyl group, naphthyl group, anthracenyl group (or anthracene group), phenanthrenyl group (or phenanthrene group), biphenyl group, terphenyl group, pyrenyl group (or pyrene group), perylenyl group (or perylene group), triphenylenyl group (or triphenylene group) and the like.

Examples of the optionally substituted heteroaryl group (or the heteroaromatic group) include:

sulfur-containing heteroaryl groups such as thiophenyl group (thiophene group or thienyl group), thienylenyl group (or thiophenediyl group), benzothienyl group, dibenzothienyl group, phenyldibenzothienylenyl group and dibenzothienylenylphenyl group;

oxygen-containing heteroaryl groups such as furanyl group (or furan group), benzofuranyl group, dibenzofuranyl group, phenyldibenzofuranyl group and dibenzofuranylphenyl group;

nitrogen-containing heteroaryl groups such as pyridyl group (or pyridine group), pyridylenyl group (or pyridinediyl group), pyrimidinyl group (or pyrimidine group), pyrazyl group (or pyrazine group), quinolyl group (or quinoline group), isoquinolyl group (or isoquinoline group), carbazolyl group (or carbazole group), 9-phenylcarbazolyl group, acridinyl group (or acrydine group), quinazolyl group (or quinazoline group), quinoxalyl group (or quinoxaline group), 1,6-naphthyridinyl group, 1,8-naphthyridinyl group and porphyrin group (or porphyrin ring); and heteroaryl groups containing two or more heteroatoms (e.g., nitrogen and sulfur), such as benzothiazolyl group (or benzothiazole group).

There is no particular limitation on the substituent, with which the aryl group and the heteroaryl group can be substituted, as long as the objective cross-coupling reaction of the present invention can be performed.

Examples of the substituent include:

alkyl groups having 1 to 24 carbon atoms, for example, 1 to 18 carbon atoms, for example, 1 to 12 carbon atoms, for example, 1 to 8 carbon atoms (e.g., methyl group, ethyl group, n-propyl group, isopropyl group, n-butyl group, isobutyl group, tert-butyl group, pentyl group, hexyl group, octyl group, etc.), alkoxy groups having 1 to 24 carbon atoms, for example, 1 to 18 carbon atoms, for example, 1 to 12 carbon atoms, for example, 1 to 8 carbon atoms (e.g., methoxy group, ethoxy group, n-propoxy group, isopropoxy group, n-butoxy group, isobutoxy group, tert-butoxy group, pentyloxy group, hexyloxy group, octyloxy group, etc.), cycloalkyl groups having 3 to 24 carbon atoms, for example, 3 to 18 carbon atoms, for example, 3 to 12 carbon atoms, for example, 3 to 8 carbon atoms (e.g., cyclopropyloxy group, cyclobutyloxy group, cyclopentyloxy group, cyclohexyloxy group, etc.), alkenyl groups having 1 to 24 carbon atoms, for example, 1 to 18 carbon atoms, for example, 1 to 12 carbon atoms, for example, 1 to 8 carbon atoms (e.g., ethenyl group, propenyl group, butenyl group, pentenyl group, hexenyl group, octenyl group, etc.), alkynyl groups having 1 to 24 carbon atoms, for example, 1 to 18 carbon atoms, for example, 1 to 12 carbon atoms, for example, 1 to 8 carbon atoms (e.g., ethynyl group, propynyl group, butynyl group, pentynyl group, hexynyl group, octynyl group, etc.), aryl groups having 5 to 24 carbon atoms, for example, 5 to 18 carbon atoms, for example, 5 to 12 carbon atoms, for example, 5 to 8 carbon atoms (e.g., phenyl group, naphthyl group, biphenyl group, etc.), aryloxy groups having 5 to 24 carbon atoms, for example, 5 to 18 carbon atoms, for example, 5 to 12 carbon atoms, for example, 5 to 8 carbon atoms (e.g., phenoxy group, naphthyloxy group, biphenyloxy group, etc.), heteroaryl groups having 4 to 24 carbon atoms, for example, 1 to 18 carbon atoms, for example, 1 to 12 carbon atoms, for example, 1 to 8 carbon atoms (e.g., thiophenyl group, furanyl group, carbazole group, benzothiophenyl group, benzofuranyl group, indolyl group, pyrrolyl group, pyridyl group, etc.), acyl groups having 1 to 24 carbon atoms, for example, 1 to 18 carbon atoms, for example, 1 to 12 carbon atoms, for example, 1 to 8 carbon atoms (e.g., acetyl group, propionyl group, butanoyl group, pentanoyl group, heptanoyl group, group in which a carbonyl group included in the acyl group is substituted with an ester group or an amide group, etc.), amino groups having 1 to 24 carbon atoms, for example, 1 to 18 carbon atoms, for example, 1 to 12 carbon atoms, for example, 1 to 8 carbon atoms (e.g., diphenylamino group, dimethylamino group, etc.), fluorine (including partial fluorine substitution and complete fluorine substitution), cyano group and nitro group.

The substituents may be crosslinked to each other, and the entire substituent may form a cyclic structure (an aromatic group). Further, the above-mentioned substituent may be further substituted with the above-mentioned substituent.

The aromatic amino compound (2-1) is more specifically represented, for example, by the general formula (II-1):

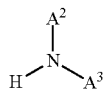

II-1 wherein $A^2$ and $A^3$ are each independently selected from hydrogen, an optionally substituted aryl group (or an aromatic hydrocarbon group) and an optionally substituted heteroaryl group (or a heteroaromatic group), $A^2$ and $A^3$ are not simultaneously hydrogen, and $A^2$ and $A^3$ may be bonded to each other.

In the formula (II-1), $A^2$ and $A^3$ are selected from hydrogen, an optionally substituted aryl group and an optionally substituted heteroaryl group, but are not simultaneously hydrogen.

The optionally substituted aryl group and the optionally substituted heteroaryl group can include the above-mentioned optionally substituted aryl group and optionally substituted heteroaryl group.

In the formula (II-1), the substituent in the optionally substituted aryl group and the optionally substituted heteroaryl group can be, for example, the above-mentioned substituent.

The substituents may be crosslinked to each other, and the entire substituent may form a cyclic structure (an aromatic group). Further, the above-mentioned substituent may be further substituted with the above-mentioned substituent.

It is possible to more specifically exemplify, as $A^2$ and $A^3$ of the aromatic amino compound (2-1), for example, the following groups:

naphthyl groups such as naphthyl group, an aryl (e.g., phenyl, etc.) naphthyl group, a naphthyl group having an alkylene (e.g., ethylene, etc.) crosslink, and a naphthyl group having an arylene (e.g., phenylene, etc.) crosslink;

phenanthrenyl groups;

anthracenyl groups such as anthracenyl group, an aryl (e.g., phenyl, etc.) anthracenyl group, a diaryl (e.g., dinaphthyl, etc.) anthracenyl group, and a diarylboryl (e.g., bis(trialkylphenyl)boryl, etc.) anthracenyl group;

pyrenyl groups such as pyrenyl group and an alkyl (e.g., t-butyl, etc.) pyrenyl group;

biphenyl groups such as biphenyl group, and a biphenyl group having an alkylene (e.g., propyrene, isopropyrene, etc.) crosslink;

terphenyl groups such as terphenyl group and a tetraaryl (e.g., tetraphenyl, etc.) terphenyl group;

triphenylenyl groups;

phenyl groups such as a 2-aryl (e.g., phenyl, etc.) ethenylphenyl group, a 1,2,2-triaryl (e.g., triphenyl, etc.) ethenylphenyl group, a 2-aryl (e.g., phenyl, etc.) ethynylphenyl group, phenyl group, an alkyl (e.g., methyl) phenyl group, a dialkyl (e.g., dimethyl) phenyl group, an alkoxy (e.g., methoxy) phenyl group, a dialkylamino (e.g., dimethylamino) phenyl group, a diaryl (e.g., diphenyl) aminophenyl group, a perfluoroalkyl (e.g., trifluoromethyl) phenyl group, an alkyl (e.g., ethyl) oxycarbonylphenyl group, and an alkanoyl (e.g., acyl) phenyl group;

aryl (e.g., phenyl, etc.)-substituted carbazolyl groups;

anthracene-9.10-dione groups, and aryl (e.g., phenyl, etc.)-substituted thienyl groups.

It is possible to use, as the aromatic amino compound (2-1), commercially available compounds.

In the present disclosure, the diboronic acid ester or the like (2-2) is not particularly limited as long as it has a B—B bond and undergoes a cross-coupling reaction with the above-mentioned aromatic compound (1) having a leaving group to give a cross-coupling product in which a B—C bond is formed.

In the present disclosure, the diboronic acid ester or the like (2-2) includes diboronic acid monoester, diboronic acid and the like, and includes, for example, tetrahydroxydiborane.

Examples of the diboronic acid ester or the like (2-2) include a diboronic acid alkyl ester, a diboronic acid alkylene glycol ester, a diboronic acid aryl ester, diboronic acid arylene glycol ester and tetrahydroxydiborane.

In the embodiment of the present invention, the diboronic acid esters or the like (2-2) (including an ester and an acid thereof) can be more specifically represented, for example, by the general formula (II-2):

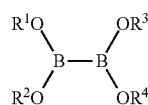

II-2 wherein $R^1$ to $R^4$ are each independently selected from hydrogen, an optionally substituted alkyl group and an optionally substituted aryl group (or an aromatic hydrocarbon group), $R^1$ and $R^2$ may be bonded to each other, and $R^3$ and $R^4$ may be bonded to each other.

In the formula (II-2), $R^1$ to $R^4$ are each independently selected from hydrogen, an optionally substituted alkyl group and an optionally substituted aryl group, $R^1$ and $R^2$ may be bonded to each other, and $R^3$ and $R^4$ may be bonded to each other. Further, $R^1$ and $R^2$ may combine together to form a cyclic structure, and $R^3$ and $R^4$ may combine together to form a cyclic structure. The cyclic structure may be an aromatic group. For example, 1,2-phenylene group and the like can be exemplified.

Examples of the optionally substituted alkyl group include methyl group, ethyl group, propyl group, isopropyl group, butyl group, isobutyl group, t-butyl group and the like. Further, two alkyl groups may be bonded, and examples of $R^1$-$R^2$ and $R^3$-$R^4$ include ethylene group, 1,1,2,2-tetramethylethylene group, 2,2-dimethylpropyrene group, hexylene group (or 1,1,3-trimethylpropyrene group) and the like.

The optionally substituted aryl group is selected, for example, from phenyl group, naphthyl group, biphenyl group and the like.

The substituent, with which the alkyl group and the aryl group may be substituted, can be selected from an alkyl group, an aryl group, an alkoxy group, an aryloxy group and the like. The substituents may be crosslinked to each other. The above-mentioned substituent may be further substituted with the above-mentioned substituent.

More specifically, examples of the diboronic acid ester or the like includes bis(pinacolato)diboron), bis(neopentyl glycolate)diboron), bis(hexylene glycolato)diboron), bis(catecholato)diboron and the like.

It is possible to use, as the diboronic acid ester or the like (2-2), commercially available products.

In the present disclosure, the aromatic boronic acid or the like (2-3) (including an acid and an ester thereof) is not particularly limited as long as it has a B—C bond and has an aromatic group, and undergoes a cross-coupling reaction with the above-mentioned aromatic compound (1) having a leaving group to give a cross-coupling product in which a C—C bond is formed. In the present disclosure, the aromatic boronic acid or the like (2-3) includes both an aromatic boronic acid and an aromatic boronic acid ester. Examples of the aromatic boronic acid ester include an aromatic boronic acid alkyl ester, an aromatic boronic acid alkylene glycol ester, an aromatic boronic acid aryl ester and an aromatic boronic acid arylene glycol ester.

The aromatic group can be selected, for example, from an optionally substituted aryl group (or an aromatic hydrocarbon group) and an optionally substituted heteroaryl group (or a heteroaromatic group).

Examples of the optionally substituted aryl group (or the aromatic hydrocarbon group) include phenyl group, naphthyl group, anthracenyl group (or anthracene group), phenanthrenyl group (or phenanthrene group), biphenyl group, terphenyl group, pyrenyl group (or pyrene group), perylenyl group (or perylene group), triphenylenyl group (or triphenylene group) and the like.

Examples of the optionally substituted heteroaryl group (or the heteroaromatic group) include:

sulfur-containing heteroaryl groups such as thiophenyl group (thiophene group or thienyl group), thienylenyl group (or thiophenediyl group), benzothienyl group, dibenzothienyl group, phenyldibenzothienylenyl group and dibenzothienylenylphenyl group;

oxygen-containing heteroaryl groups such as furanyl group (or furan group), benzofuranyl group, dibenzofuranyl group, phenyldibenzofuranyl group and dibenzofuranylphenyl group;

nitrogen-containing heteroaryl groups such as pyridyl group (or pyridine group), pyridylenyl group (or pyridinediyl group), pyrimidinyl group (or pyrimidine group), pyrazyl group (or pyrazine group), quinolyl group (or quinoline group), isoquinolyl group (or isoquinoline group), carbazolyl group (or carbazole group), 9-phenylcarbazolyl group, acridinyl group (or acrydine group), quinazolyl group (or quinazoline group), quinoxalyl group (or quinoxaline group), 1,6-naphthyridinyl group, 1,8-naphthyridinyl group and porphyrin group (or porphyrin ring); and heteroaryl groups containing two or more heteroatom (e.g., nitrogen and sulfur), such as benzothiazolyl group (or benzothiazole group).

There is no particular limitation on the substituent, with which the aryl group and the heteroaryl group can be substituted, as long as the objective cross-coupling reaction of the present invention can be performed.

Examples of the substituent include:

alkyl groups having 1 to 24 carbon atoms, for example, 1 to 18 carbon atoms, for example, 1 to 12 carbon atoms, for example, 1 to 8 carbon atoms (e.g., methyl group, ethyl group, n-propyl group, isopropyl group, n-butyl group, isobutyl group, tert-butyl group, pentyl group, hexyl group, octyl group, etc.), alkoxy groups having 1 to 24 carbon atoms, for example, 1 to 18 carbon atoms, for example, 1 to 12 carbon atoms, for example, 1 to 8 carbon atoms (e.g., methoxy group, ethoxy group, n-propoxy group, isopropoxy group, n-butoxy group, isobutoxy group, tert-butoxy group, pentyloxy group, hexyloxy group, octyloxy group, etc.), cycloalkyl groups having 3 to 24 carbon atoms, for example, 3 to 18 carbon atoms, for example, 3 to 12 carbon atoms, for example, 3 to 8 carbon atoms (e.g., cyclopropyloxy group, cyclobutyloxy group, cyclopentyloxy group, cyclohexyloxy group, etc.), alkenyl groups having 1 to 24 carbon atoms, for example, 1 to 18 carbon atoms, for example, 1 to 12 carbon atoms, for example, 1 to 8 carbon atoms (e.g., ethenyl group, propenyl group, butenyl group, pentenyl group, hexenyl group, octenyl group, etc.), alkynyl groups having 1 to 24 carbon atoms, for example, 1 to 18 carbon atoms, for example, 1 to 12 carbon atoms, for example, 1 to 8 carbon atoms (e.g., ethynyl group, propynyl group, butynyl group, pentynyl group, hexynyl group, octynyl group, etc.), aryl groups having 5 to 24 carbon atoms, for example, 5 to 18 carbon atoms, for example, 5 to 12 carbon atoms, for example, 5 to 8 carbon atoms (e.g., phenyl group, naphthyl group, biphenyl group, etc.), aryloxy groups having 5 to 24 carbon atoms, for example, 5 to 18 carbon atoms, for example, 5 to 12 carbon atoms, for example, 5 to 8 carbon atoms (e.g., phenoxy group, naphthyloxy group, biphenyloxy group, etc.), heteroaryl groups having 4 to 24 carbon atoms, for example, 1 to 18 carbon atoms, for example, 1 to 12 carbon atoms, for example, 1 to 8 carbon atoms (e.g., thiophenyl group, furanyl group, carbazole group, benzothiophenyl group, benzofuranyl group, indolyl group, pyrrolyl group, pyridyl group, etc.), acyl groups having 1 to 24 carbon atoms, for example, 1 to 18 carbon atoms, for example, 1 to 12 carbon atoms, for example, 1 to 8 carbon atoms (e.g., acetyl group, propionyl group, butanoyl group, pentanoyl group, heptanoyl group, a group in which a carbonyl group included in the acyl group is substituted with an ester group or an amide group, etc.), amino groups having 1 to 24 carbon atoms, for example, 1 to 18 carbon atoms, for example, 1 to 12 carbon atoms, for example, 1 to 8 carbon atoms (e.g., diphenylamino group, dimethylamino group, etc.), and fluorine (including partial fluorine substitution and complete fluorine substitution), cyano group and nitro group.

In the embodiment of the present invention, the aromatic boronic acid or the like (2-3) (including an acid and an ester thereof) can be more specifically represented, for example, by the general formula (II-3):

II-3 wherein $R^5$ to $R^6$ are each independently selected from hydrogen, an optionally substituted alkyl group and an optionally substituted aryl group, and $R^5$ and $R^6$ may be bonded to each other, and $A^4$ is selected from an optionally substituted aryl group and an optionally substituted heteroaryl group.

In the formula (II-3), $R^5$ to $R^6$ are each independently selected from hydrogen, an optionally substituted alkyl group and an optionally substituted aryl group (or an aromatic hydrocarbon group), $R^5$ and $R^6$ may be bonded to each other. Further, $R^5$ and $R^6$ may combine to form a cyclic structure. The cyclic structure may be an aromatic group. For example, a 1,2-phenylene group and the like can be exemplified.

Examples of the optionally substituted alkyl group include methyl group, ethyl group, propyl group, isopropyl group, butyl group, isobutyl group, t-butyl group and the like. Further, two alkyl groups may be bonded, and examples of $R^5$-$R^6$ include an ethylene group, 1,1,2,2-tetramethylethylene group (pinacolato group), neopentyl glycolate group and propyrene group.

The optionally substituted aryl group is selected, for example, from phenyl group, naphthyl group, biphenyl group and the like.

Both the alkyl group and the aryl group are optionally substituted. The substituent can be selected from an alkyl group, an aryl group, an alkoxy group, an aryloxy group and the like. The substituents may be crosslinked to each other. The substituent can be further substituted.

In the formula (II-3), $A^4$ is not particularly limited as long as it is selected from an optionally substituted aryl group and an optionally substituted heteroaryl group, and a cross-coupling reaction can be performed.

The optionally substituted aryl group and the optionally substituted heteroaryl group can include the above-mentioned optionally substituted aryl group and optionally substituted heteroaryl group.

In the formula (II-3), the substituent of the optionally substituted aryl group and the optionally substituted heteroaryl group can be, for example, the above-mentioned substituent.

Further, the substituent may be further substituted with the above-mentioned substituent.

It is possible to more specifically exemplify, as $A^4$ of the aromatic boronic acid (2-3), for example, the following groups:

naphthyl groups such as naphthyl group, an aryl (e.g., phenyl) naphthyl group, a naphthyl group having an alkylene (e.g., ethylene) crosslink, and a naphthyl group having an arylene (e.g., phenylene) crosslink;

phenanthrenyl groups;

anthracenyl groups such as anthracenyl group, an aryl (e.g., phenyl) anthracenyl group, a diaryl (e.g., dinaphthyl)

anthracenyl group, and a diarylboryl (e.g., bis(trialkylphenyl)boryl) anthracenyl group;

pyrenyl groups such as pyrenyl group and an alkyl (e.g., t-butyl) pyrenyl group;

biphenyl groups such as biphenyl group, and a biphenyl group having an alkylene (e.g., propyrene, isopropyrene) crosslink;

terphenyl groups such as terphenyl group and a tetraaryl (e.g., tetraphenyl) terphenyl group;

triphenylenyl groups;

phenyl groups such as a 2-aryl (e.g., phenyl) ethenylphenyl group, a 1,2,2-triaryl (e.g., triphenyl) ethenylphenyl group, a 2-aryl (e.g., phenyl) ethynylphenyl group, phenyl group, an alkyl (e.g., methyl) phenyl group, a dialkyl (e.g., dimethyl) phenyl group, an alkoxy (e.g., methoxy) phenyl group, a dialkylamino (e.g., dimethylamino) phenyl group, a diaryl (e.g., diphenyl) aminophenyl group, a perfluoroalkyl (e.g., trifluoromethyl) phenyl group, an alkyl (e.g., ethyl) oxycarbonylphenyl group, and an alkanoyl (e.g., acyl) phenyl group;

aryl (e.g., phenyl)-substituted carbazolyl groups;

anthracene-9.10-dione groups, and thienyl groups and aryl (e.g., phenyl) thienyl groups.

It is possible to use, as the aromatic boronic acid (2-3), commercially available compounds.

In the present disclosure, the aromatic compound (2-4) having a hydroxyl group is not particularly limited as long as it has a H—O bond and has an aromatic group, and undergoes a cross-coupling reaction with the above-mentioned aromatic compound (1) having a leaving group to give a cross-coupling reaction product in which an O—C bond is formed.

The aromatic group can be selected, for example, from an optionally substituted aryl group (or an aromatic hydrocarbon group) and an optionally substituted heteroaryl group (or a heteroaromatic group).

Examples of the optionally substituted aryl group (or the aromatic hydrocarbon group) include phenyl group, naphthyl group, anthracenyl group (or anthracene group), phenanthrenyl group (or phenanthrene group), biphenyl group, terphenyl group, pyrenyl group (or pyrene group), perylenyl group (or perylene group), triphenylenyl group (or triphenylene group) and the like.

Examples of the optionally substituted heteroaryl group (or the heteroaromatic group) include:

sulfur-containing heteroaryl groups such as thiophenyl group (thiophene group or thienyl group), thienylenyl group (or thiophenediyl group), benzothienyl group, dibenzothienyl group, phenyldibenzothienylenyl group and dibenzothienylenylphenyl group;

oxygen-containing heteroaryl groups such as furanyl group (or furan group), benzofuranyl group, dibenzofuranyl group, phenyldibenzofuranyl group and dibenzofuranylphenyl group;

nitrogen-containing heteroaryl groups such as pyridyl group (or pyridine group), pyridylenyl group (or pyridinediyl group), pyrimidinyl group (or pyrimidine group), pyrazyl group (or pyrazine group), quinolyl group (or quinoline group), isoquinolyl group (or isoquinoline group), carbazolyl group (or carbazole group), 9-phenylcarbazolyl group, acridinyl group (or acrydine group), quinazolyl group (or quinazoline group), quinoxalyl group (or quinoxaline group), 1,6-naphthyridinyl group, 1,8-naphthyridinyl group and porphyrin group (or porphyrin ring); and heteroaryl groups containing two or more heteroatoms (e.g., nitrogen and sulfur), such as benzothiazolyl group (or benzothiazole group).

There is no particular limitation on the substituent, with which the aryl group and the heteroaryl group can be substituted, as long as the objective cross-coupling reaction of the present invention can be performed.

Examples of the substituent include:

alkyl groups having 1 to 24 carbon atoms, for example, 1 to 18 carbon atoms, for example, 1 to 12 carbon atoms, for example, 1 to 8 carbon atoms (e.g., methyl group, ethyl group, n-propyl group, isopropyl group, n-butyl group, isobutyl group, tert-butyl group, pentyl group, hexyl group, octyl group, etc.), alkoxy groups having 1 to 24 carbon atoms, for example, 1 to 18 carbon atoms, for example, 1 to 12 carbon atoms, for example, 1 to 8 carbon atoms (e.g., methoxy group, ethoxy group, n-propoxy group, isopropoxy group, n-butoxy group, isobutoxy group, tert-butoxy group, pentyloxy group, hexyloxy group, octyloxy group, etc.), cycloalkyl groups having 3 to 24 carbon atoms, for example, 3 to 18 carbon atoms, for example, 3 to 12 carbon atoms, for example, 3 to 8 carbon atoms (e.g., cyclopropyloxy group, cyclobutyloxy group, cyclopentyloxy group, cyclohexyloxy group, etc.), alkenyl groups having 1 to 24 carbon atoms, for example, 1 to 18 carbon atoms, for example, 1 to 12 carbon atoms, for example, 1 to 8 carbon atoms (e.g., ethenyl group, propenyl group, butenyl group, pentenyl group, hexenyl group, octenyl group, etc.), alkynyl groups 1 to 24 carbon atoms, for example, 1 to 18 carbon atoms, for example, 1 to 12 carbon atoms, for example, 1 to 8 carbon atoms (e.g., ethynyl group, propynyl group, butynyl group, pentynyl group, hexynyl group, octynyl group, etc.), aryl groups having 5 to 24 carbon atoms, for example, 5 to 18 carbon atoms, for example, 5 to 12 carbon atoms, for example, 5 to 8 carbon atoms (e.g., phenyl group, naphthyl group, biphenyl group, etc.), aryloxy groups having 5 to 24 carbon atoms, for example, 5 to 18 carbon atoms, for example, 5 to 12 carbon atoms, for example, 5 to 8 carbon atoms (e.g., phenoxy group, naphthyloxy group, biphenyloxy group, etc.), heteroaryl groups having 4 to 24 carbon atoms, for example, 1 to 18 carbon atoms, for example, 1 to 12 carbon atoms, for example, 1 to 8 carbon atoms (e.g., thiophenyl group, furanyl group, carbazole group, benzothiophenyl group, benzofuranyl group, indolyl group, pyrrolyl group, pyridyl group, etc.), acyl groups having 1 to 24 carbon atoms, for example, 1 to 18 carbon atoms, for example, 1 to 12 carbon atoms, for example, 1 to 8 carbon atoms (e.g., acetyl group, propionyl group, butanoyl group, pentanoyl group, heptanoyl group, a group in which a carbonyl group included in the acyl group is substituted with an ester group or an amide group, etc.), amino groups having 1 to 24 carbon atoms, for example, 1 to 18 carbon atoms, for example, 1 to 12 carbon atoms, for example, 1 to 8 carbon atoms (e.g., diphenylamino group, dimethylamino group, etc.), and fluorine (including partial fluorine substitution and complete fluorine substitution), cyano group and nitro group.

In the embodiment of the present invention, the aromatic compound (2-4) having a hydroxyl group can be more specifically represented, for example, by the general formula (II-4):

$$HO-(C_mH_{2m})-A^5$$

wherein $A^5$ is selected from an optionally substituted aryl group and an optionally substituted heteroaryl group, and m is an integer of 0 to 20.

In the formula (II-4), m is an integer of 0 to 20, m is preferably 10 or less, and more preferably 4 or less. $A^5$ is not particularly limited as long as it can be selected from an optionally substituted aryl group and an optionally substituted heteroaryl group, and a cross-coupling reaction can be performed.

The optionally substituted aryl group and the optionally substituted heteroaryl group can include the above-mentioned optionally substituted aryl group and optionally substituted heteroaryl group.

In the formula (II-4), the substituent of the optionally substituted aryl group and the optionally substituted heteroaryl group can be, for example, the above-mentioned substituent.

Further, the substituent may be further substituted with the above-mentioned substituent.

It is possible to more specifically exemplify, as $A^5$ of the aromatic compound (2-4) having a hydroxyl group, for example, the following groups:

naphthyl groups such as naphthyl group, an aryl (e.g., phenyl) naphthyl group, a naphthyl group having an alkylene (e.g., ethylene) crosslink, and a naphthyl group having an arylene (e.g., phenylene) crosslink;

phenanthrenyl groups;

anthracenyl groups such as anthracenyl group, an aryl (e.g., phenyl)anthracenyl group, a diaryl (e.g., dinaphthyl) anthracenyl group, and a diarylboryl (e.g., bis(trialkylphenyl)boryl) anthracenyl group;

pyrenyl groups such as pyrenyl group, an alkyl (e.g., t-butyl) pyrenyl group;

biphenyl groups such as biphenyl group, and a biphenyl group having an alkylene (e.g., propyrene, isopropyrene) crosslink;

terphenyl groups such as terphenyl group, and a tetraaryl (e.g., tetraphenyl) terphenyl group;

triphenylenyl groups;

phenyl groups such as a 2-aryl (e.g., phenyl) ethenylphenyl group, a 1,2,2-triaryl (e.g., triphenyl) ethenylphenyl group, a 2-aryl (e.g., phenyl) ethynylphenyl group, phenyl group, an alkyl (e.g., methyl) phenyl group, a dialkyl (e.g., dimethyl) phenyl group, an alkoxy (e.g., methoxy) phenyl group, a dialkylamino (e.g., dimethylamino) phenyl group, a diaryl (e.g., diphenyl) aminophenyl group, a perfluoroalkyl (e.g., trifluoromethyl) phenyl group, an alkyl (e.g., ethyl) oxycarbonylphenyl group, and an alkanoyl (e.g., acyl) phenyl group;

aryl (e.g., phenyl)carbazolyl groups;

anthracene-9.10-dione groups, and thienyl groups and aryl (e.g., phenyl) thienyl groups.

It is possible to use, as the aromatic compound (2-4) having a hydroxyl group, commercially available compounds.

In the present disclosure, the aromatic compound (2-5) having a thiol group is not particularly limited as long as it has an H—S bond and has an aromatic group, and undergoes a cross-coupling reaction with the above-mentioned aromatic compound (1) having a leaving group to give a cross-coupling reaction product in which an S—C bond is formed.

The aromatic group can be selected, for example, from an optionally substituted aryl group (or aromatic hydrocarbon group) and an optionally substituted heteroaryl group (or a heteroaromatic group).

Examples of the optionally substituted aryl group (or the aromatic hydrocarbon group) include phenyl group, naphthyl group, anthracenyl group (or anthracene group), phenanthrenyl group (or phenanthrene group), biphenyl group, terphenyl group, pyrenyl group (or pyrene group), perylenyl group (or perylene group), triphenylenyl group (or triphenylene group) and the like.

Examples of the optionally substituted heteroaryl group (or the heteroaromatic group) include:

sulfur-containing heteroaryl groups such as thiophenyl group (thiophene group or thienyl group), thienylenyl group (or thiophenediyl group), benzothienyl group, dibenzothienyl group, phenyldibenzothienylenyl group and dibenzothienylenylphenyl group, oxygen-containing heteroaryl groups such as furanyl group (or furan group), benzofuranyl group, dibenzofuranyl group, phenyldibenzofuranyl group and dibenzofuranylphenyl group;

nitrogen-containing heteroaryl groups such as pyridyl group (or pyridine group), pyridylenyl group (or pyridinediyl group), pyrimidinyl group (or pyrimidine group), pyrazyl group (or pyrazine group), quinolyl group (or quinoline group), isoquinolyl group (or isoquinoline group), carbazolyl group (or carbazole group), 9-phenylcarbazolyl group, acridinyl group (or acrydine group), quinazolyl group (or quinazoline group), quinoxalyl group (or quinoxaline group), 1,6-naphthyridinyl group, 1,8-naphthyridinyl group and porphyrin group (or porphyrin ring); and heteroaryl groups containing two or more heteroatoms (e.g., nitrogen and sulfur), such as benzothiazolyl group (or benzothiazole group).

There is no particular limitation on the substituent, with which the aryl group and the heteroaryl group can be substituted, as long as the objective cross-coupling reaction of the present invention can be performed.

Examples of the substituent include:

alkyl groups having 1 to 24 carbon atoms, for example, 1 to 18 carbon atoms, for example, 1 to 12 carbon atoms, for example, 1 to 8 carbon atoms (e.g., methyl group, ethyl group, n-propyl group, isopropyl group, n-butyl group, isobutyl group, tert-butyl group, pentyl group, hexyl group, octyl group, etc.), alkoxy groups having 1 to 24 carbon atoms, for example, 1 to 18 carbon atoms, for example, 1 to 12 carbon atoms, for example, 1 to 8 carbon atoms (e.g., methoxy group, ethoxy group, n-propoxy group, isopropoxy group, n-butoxy group, isobutoxy group, tert-butoxy group, pentyloxy group, hexyloxy group, octyloxy group, etc.), cycloalkyl groups having 3 to 24 carbon atoms, for example, 3 to 18 carbon atoms, for example, 3 to 12 carbon atoms, for example, 3 to 8 carbon atoms (e.g., cyclopropyloxy group, cyclobutyloxy group, cyclopentyloxy group, cyclohexyloxy group, etc.), alkenyl groups having 1 to 24 carbon atoms, for example, 1 to 18 carbon atoms, for example, 1 to 12 carbon atoms, for example, 1 to 8 carbon atoms (e.g., ethenyl group, propenyl group, butenyl group, pentenyl group, hexenyl group, octenyl group, etc.), alkynyl groups having 1 to 24 carbon atoms, for example, 1 to 18 carbon atoms, for example, 1 to 12 carbon atoms, for example, 1 to 8 carbon atoms (e.g., ethynyl group, propynyl group, butynyl group, pentynyl group, hexynyl group, octynyl group, etc.), aryl groups having 5 to 24 carbon atoms, for example, 5 to 18 carbon atoms, for example, 5 to 12 carbon atoms, for example, 5 to 8 carbon atoms (e.g., phenyl group, a naphthyl group, biphenyl group, etc.), aryloxy groups having 5 to 24 carbon atoms, for example, 5 to 18 carbon atoms, for example, 5 to 12 carbon atoms, for example, 5 to 8 carbon atoms (e.g., phenoxy group, naphthyloxy group, biphenyloxy group, etc.), heteroaryl groups having 4 to 24 carbon atoms, for example, 1 to 18 carbon atoms, for example, 1 to 12 carbon atoms, for example, 1 to 8 carbon atoms (e.g., thiophenyl group, furanyl group, carbazole group, benzothiophenyl group, benzofuranyl group, indolyl group, pyrrolyl group, pyridyl group, etc.), acyl groups having 1 to 24 carbon atoms, for example, 1 to 18 carbon atoms, for example, 1 to 12 carbon atoms, for example, 1 to 8 carbon atoms (e.g., acetyl group, propionyl group, butanoyl group, pentanoyl group, heptanoyl group, a group in which a carbonyl group included in the acyl group is substituted with an ester group or an amide group, etc.), amino groups having 1 to 24 carbon atoms, for example, 1 to 18 carbon atoms, for example, 1 to 12 carbon atoms, for example, 1 to 8 carbon atoms (e.g., diphenylamino group, dimethylamino group, etc.), and fluorine (including partial fluorine substitution and complete fluorine substitution), cyano group and nitro group.

In the embodiment of the present invention, the aromatic compound (2-5) having a thiol group is more specifically selected, for example, from the general formula (II-5):

$$HS-(C_pH_{2p})-A^6$$

wherein $A^6$ is selected from an optionally substituted aryl group and an optionally substituted heteroaryl group, and p is an integer of 0 to 20.

In the formula (II-5), p is an integer of 0 to 20, p is preferably 10 or less, and more preferably 4 or less. $A^5$ is not particularly limited as long as it can be selected from an optionally substituted aryl group and an optionally substituted heteroaryl group, and a cross-coupling reaction can be performed.

The optionally substituted aryl group and the optionally substituted heteroaryl group can include the above-mentioned optionally substituted aryl group and optionally substituted heteroaryl group.

In the formula (II-5), the substituent of the optionally substituted aryl group and the optionally substituted heteroaryl group can be, for example, the above-mentioned substituent.

Further, the substituent may be further substituted with the above-mentioned substituent.

It is possible to more specifically exemplify, as $A^6$ of the aromatic compound (2-5) having a thiol group, for example, the following groups:

naphthyl groups such as naphthyl group, an aryl (e.g., phenyl) naphthyl group, a naphthyl group having an alkylene (e.g., ethylene) crosslink, and a naphthyl group having an arylene (e.g., phenylene) crosslink;

phenanthrenyl groups;

anthracenyl groups such as anthracenyl group, an aryl (e.g., phenyl) anthracenyl group, a diaryl (e.g., dinaphthyl) anthracenyl group, and a diarylboryl (e.g., bis(trialkylphenyl)boryl) anthracenyl group;

pyrenyl groups such as pyrenyl group, an alkyl (e.g., t-butyl) pyrenyl group;

biphenyl groups such as biphenyl group, and a biphenyl group having an alkylene (e.g., propyrene, isopropyrene) crosslink;

terphenyl groups such as terphenyl group, tetraaryl (e.g., tetraphenyl)terphenyl group;

triphenylenyl groups;

phenyl groups such as a 2-aryl (e.g., phenyl) ethenylphenyl group, a 1,2,2-triaryl (e.g., triphenyl) ethenylphenyl group, a 2-aryl (e.g., phenyl) ethynylphenyl group, phenyl group, an alkyl (e.g., methyl) phenyl group, a dialkyl (e.g., dimethyl) phenyl group, an alkoxy (e.g., methoxy) phenyl group, a dialkylamino (e.g., dimethylamino) phenyl group, a diaryl (e.g., diphenyl) aminophenyl group, a perfluoroalkyl (e.g., trifluoromethyl) phenyl group, an alkyl (e.g., ethyl) oxycarbonylphenyl group, and an alkanoyl (e.g., acyl) phenyl group;

aryl (e.g., phenyl) carbazolyl groups;

anthracene-9.10-dione groups, and thienyl groups and aryl (e.g., phenyl) thienyl groups.

It is possible to use, as the aromatic compound (2-5) having a thiol group, commercially available compounds.

The cross-coupling reaction method of the embodiment of the present invention comprises:

<3> performing a cross-coupling reaction of the compound (1) with the compound (2) in the presence of a palladium catalyst, a base and a compound (4) having a carbon-carbon double bond or a carbon-carbon triple bond, in the absence of a solvent.

In the embodiment of the present invention, the palladium catalyst is not particularly limited as long as it is usually used in a cross-coupling reaction, and the objective cross-coupling reaction between the above-mentioned compound (1) and compound (2) of the present invention can be progressed in the absence of a solvent.

In the embodiment of the present invention, examples of the palladium catalyst include divalent palladium compounds such as palladium(II) acetate, palladium(II) chloride, palladium(II) bromide, palladium(II) acetylacetonate, dichlorobis(benzonitrile)palladium(II), dichlorobis(acetonitrile)palladium(II), dichlorobis(triphenylphosphine)palladium(II), dichlorotetraamminepalladium(II), dichloro(cyclooctadi-1,5-diene)palladium(II) and palladium(II) trifluoroacetate; and zero-valent palladium compounds such as tris(dibenzilidenacetone)dipalladium(0), tris(dibenzilidenacetone)dipalladium(0) chloroform complex and tetrakis(triphenylphosphine)palladium(0).

The palladium catalysts can be used alone or in combination, respectively.

It is possible to use, as the palladium catalyst, commercially available products.

The palladium catalyst can be allowed to coexist with a coordinating compound such as a phosphine compound. The phosphine compound is not particularly limited as long as it is used in the objective cross-coupling reaction of the present invention.

It is possible to exemplify, as the phosphine compound, for example, arylphosphines such as triphenylphosphine, tri(o-tolyl)phosphine and tri(mesityl)phosphine; and alkylphosphines such as tri(tert-butyl)phosphine, tri(cyclohexyl)phosphine and tri(isopropyl)phosphine.

It is also possible to exemplify, as the phosphine compound, for example, arylalkylphosphines having both an aryl group and an alkyl group, such as DavePhos (see the following formula) and tBuBrettPhos (see the following formula). The alkylphosphines can include arylalkylphosphines. Further, the alkyl group includes a cycloalkyl group.

Formula 4

DavePhos:

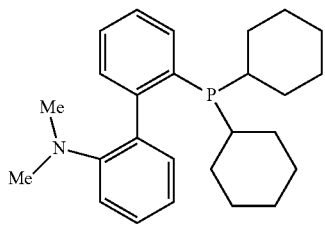

tBuBrettPhos:

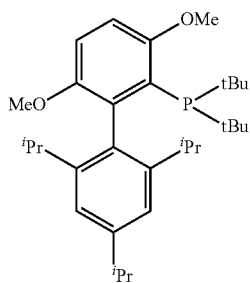

The phosphine compound preferably includes alkylphosphines.

The phosphine compounds can be used alone or in combination, respectively.

It is possible to use, as the phosphine compound, commercially available products.

In the embodiment of the invention, the base is not particularly limited as long as it is used in a cross-coupling reaction, and the objective cross-coupling reaction between the above-mentioned compound (1) and compound (2) of the present invention can be progressed in the absence of a solvent.

It is possible to exemplify, as the base, for example:

inorganic bases such as sodium hydroxide, potassium hydroxide, sodium carbonate, potassium carbonate, rubidium carbonate, cesium carbonate, potassium phosphate, sodium phosphate, potassium fluoride and cesium fluoride;

alkali metal alkoxides such as sodium methoxide, sodium ethoxide, potassium methoxide, potassium ethoxide, lithium tert-butoxide, sodium tert-butoxide and potassium tert-butoxide; and organic bases such as triethylamine, tributylamine, pyridine, diazabicycloundecene and diazabicyclononene.

The bases can be used alone or in combination, respectively.

It is possible to use, as the base, commercially available products.

In the embodiment of the present invention, the compound (4) having a carbon-carbon double bond or a carbon-carbon triple bond refers to a compound having at least one carbon-carbon double bond or at least one carbon-carbon triple bond, and may be either chain or linear (excluding aromatic), and is not particularly limited as long as the objective cross-coupling reaction between the above-mentioned compound (1) and compound (2) of the present invention can be progressed in the absence of a solvent. A compound corresponding to the above-mentioned compound (1), compound (2), palladium catalyst, coordinating compound or the base is not included in the compound (4).

The compound (4) preferably has 5 to 24 carbon atoms to promote the cross-coupling reaction. The number of carbon atoms of the compound (4) can be 5 to 18, 5 to 12, 6 to 10, or 6 to 8.

Examples of the chain compound (4) having one carbon-carbon double bond include hexene, heptene, octene, nonene, decene and the like.

Examples of the cyclic compound (4) having one carbon-carbon double bond include cyclohexene, cycloheptene, cyclooctene, cyclodecene and the like.

Examples of the chain compound (4) having two carbon-carbon double bonds include hexadiene, heptadiene, octadiene, nonadiene, decadiene and the like.

Examples of the cyclic compound (4) having two carbon-carbon double bonds include cyclohexadiene, cycloheptadiene, cyclooctadiene, cyclodecadiene and the like.

Examples of the chain compound (4) having one carbon-carbon triple bond include hexyne, heptyne, octyne, decyne and the like.

Examples of the cyclic compound (4) having one carbon-carbon triple bond include cyclooctyne, cyclodecyne and the like.

The compound (4) is preferably chain or monocyclic.

In the embodiment of the present invention, the cross-coupling reaction of the compound (1) with the compound (2) can be performed by mixing (preferably shaking) in the absence of a solvent, in the presence of the palladium catalyst, the base and the compound (4).

Either or both of the compound (1) and the compound (2) may be solid at 40° C.

In the present disclosure, solvent-free (or absence of solvent) usually means that the solvent usually used in cross-coupling reactions (e.g., aromatic solvents such as benzene, toluene, xylene and mesityrene; ether-based solvents such as diethyl ether, diisopropyl ether, dibutyl ether, tetrahydrofuran, dimethoxyethane and 1,4-dioxane; alcohol-based solvents such as methanol, ethanol and t-butanol; and polar solvents such as acetonitrile, dimethylformamide and dimethylacetamide) is used in an amount of up to 0.2 mL or less, 0.1 mL or less, 0.05 mL or less, 0.02 mL or less, or 0.01 mL or less, per 1 mmol of the total of the compound (1) and compound (2), and that the reaction is performed without using the solvent, substantially and actively.

Generally, in the cross-coupling reactions, 1 to 2 mL of the solvent is used per 1 mmol of the total of reaction raw materials, so that the amount of the solvent used is obviously small in the embodiment of the present invention. In the embodiment of the present invention, the reaction raw materials can usually exist in a solid state without being partially dissolved in the solvent at the start of the reaction, and in some cases, without being completely dissolved in the solvent.

The cross-coupling reaction (mixing temperature) can be usually performed at room temperature (e.g., 5 to 40° C.), and can be performed by heating as appropriate.

As the mixing method, any mixable method such as shaking, rubbing, pressing, dispersing, kneading and crushing may be used.

Mixing can be performed using, as such a device, for example:

crushers such as a ball mill, a rod mill, a jet mill and a SAG mill;

grinders such as a rotary stone mill and a bud crusher;

(horizontal axis rotation) container rotation type mixers such as horizontal cylindrical type, V type, double cone type, square cube type, S type and continuous V type mixers;

container rotation type mixers (with baffle plate blade) such as horizontal cylinder type, V type, double cone type and ball mill type mixers;

(rotary vibration) container rotary type mixers such as locking type and cross-rotary type mixers;

(horizontal axis rotation) fixed container type mixers such as ribbon type, paddle type, single shaft rotor type and bug mill type mixers;

(vertical axis rotation) fixed container type mixers such as ribbon type, screw type, planet type, turbine type, high-speed fluid type, rotating disk type and Marler type mixers;

(vibration) fixed container type mixers such as a vibration mill type mixer and a sieve;

(fluidized) fluid motion type mixers such as non-uniform fluidized bed, swirl fluidized bed, riser pipe type and jot pump type mixers; and (gravity) fluid motion type mixers such as a gravity type mixer and a static mixer. As long as the cross-coupling reaction proceeds, the method and the apparatus used are not particularly limited. Regarding the mixing device, it is possible to refer to, for example, Sakashita "Powder Mixing Process Technology", Coloring Material, 77 (2), 75-85 (2004), Table 5 and FIG. 9.

The mixing rate can also be appropriately selected.

The mixing time can also be appropriately selected. In the embodiment of the present invention, the mixing time can be, for example, 15 minutes or more, 30 minutes or more, 45 minutes or more, 60 minutes or more, 2 hours or less, 3 hours or less, 5 hours or less, or 10 hours or less.

The equivalent ratio of the compound (1) to the compound (2) (compound (1)/compound (2)) is not particularly limited as long as it is an equivalent ratio which can allow the cross-coupling reaction to proceed, and may be, for example, 10/1 to 1/10, 5/1 to 1/5, 3/1 to 1/3, or 2/1 to 1/2.

The equivalent of the base is not particularly limited as long as it is an amount which can allow the cross-coupling reaction to proceed, and can be, for example, 0.5 or more, 0.8 or more, 1.0 or more, 1.2 or more, 1.4 or more, 3 or less, 4 or less, 5 or less, or 10 or less, based on the equivalent of the compound (1).

The amount of the palladium catalyst is not particularly limited as long as it is an amount which can allow the cross-coupling reaction to proceed. For example, the amount can be 0.5 mol % or more, 0.1 mol % or more, 0.5 mol % or more, 1 mol % or more, 25 mol % or less, 20 mol % or less, 15 mol % or less, or 10 mol % or less, based on the number of mols (100%) obtained by multiplying the number of mols of the compound (1) by the valence of the compound (1).

When the phosphine compound is allowed to coexist with the palladium catalyst, a molar ratio of the phosphine compound to the palladium catalyst (phosphine compound/palladium catalyst) is not particularly limited as long as it is an molar ratio which can allow the cross-coupling reaction to proceed, and may be, for example, 10/1 to 1/10, 5/1 to 1/5, 3/1 to 1/3, or 2/1 to 1/2.

The amount of the compound (4) added is not particularly limited as long as it is an amount which can allow the cross-coupling reaction to proceed. For example, it is possible to add in the amount of 0.01 to 3 microL/mg, 0.05 to 1 microL/mg, or 0.1 to 0.5 microL/mg, based on the total mass of all reaction raw materials added to perform the cross-coupling reaction (e.g., the compound (1), the compound (2), the palladium catalyst, the base, and the phosphine compound when the phosphine compound is added).

It is possible to additionally use a conventionally known accelerator for the cross-coupling reactions in the cross-coupling reaction of the present disclosure. Examples of such accelerator include water and the like. The amount of the additional accelerator added is not particularly limited as long as it is an amount which can allow the cross-coupling reaction to proceed.

The cross-coupling reaction product thus obtained can be appropriately purified. The purification method is not particularly limited as long as the cross-coupling reaction product can be purified. It is possible to use, as the purification method, for example, a conventional method such as recrystallization and column chromatography.

The present invention provides, in another aspect, a method for producing a cross-coupling reaction product using the above cross-coupling reaction method which forms a chemical bond selected from C—N, C—B, C—C, C—O and C—S bonds.

It is possible to directly apply the formulas and terms described in the cross-coupling reaction method to the production method.

In the reaction method of the embodiment of the present invention, a remarkable improvement in reactivity was observed as compared with the case where the compound (4) is not used. Usually, when the reaction is performed in the absence of a solvent, the reactants such as the compound (1), the compound (2), the base, the palladium catalyst and the reaction product are not efficiently diffused, and in particular, the catalyst cannot be efficiently diffused, and thus the reaction is expected to be difficult to proceed.

When the palladium particles after the reaction were observed using a transmission electron microscope, it was found that the addition of the compound (4) suppressed the aggregation of the palladium catalyst. It was suggested that the compound (4) contributes to the suppression of the aggregation of the palladium catalyst and contributes to an improvement in reactivity.

The reaction method and the production method of the embodiment of the present invention are considered to exert excellent effect by this reason, but such a reason does not limit the present invention in any way.

EXAMPLES

The present invention will be described below by way of Examples and Comparative Examples. However, these Examples are merely embodiments of the invention and the present invention is in no way limited by these Examples.

Compounds used in Examples were specifically exemplified in the following Examples.

Regarding compounds used in the Examples, such as an aromatic compound (1) having a leaving group, a compound (2) which is capable of undergoing a cross-coupling reaction with the compound (1) to form C—N, C—B, C—C, C—O and C—S bonds, a palladium compound, a phosphine compound, and a compound (4) having a carbon-carbon double or triple bond, commercially available products were directly used without purification.

A cross-coupling reaction was performed at room temperature using a ball mill, Model MM400, manufactured by Retsch Co., Ltd. (changed company name to Verder Scientific Co., Ltd.).

Example 1

In a 1.5 mL stainless steel ball mill jar containing stainless steel balls having a diameter of 3 mm, 1-bromopyrene (1a) (140.6 mg, 0.5 mmol, 1.0 equiv), diphenylamine (2-1a) (84.6 mg, 0.5 mmol, 1.0 equiv) and palladium acetate (5.6 mg, 0.025 mmol, 5 mol %) were charged under the air. The ball mill jar was transferred to a glove box, and then tri-tert-butylphosphine (5.1 mg, 0.025 mmol, 5 mol %) and sodium tert-butoxide (72.1 mg, 0.75 mmol, 1.5 equiv) were added under argon atmosphere. The ball mill jar was removed from the glove box, and then 1,5-cyclooctadiene (4a) (59 microL, 0.20 microL/mg based on the total mass of the 1-bromopyrene, the diphenylamine, the palladium acetate, the tri-tert-butylphosphine and the sodium tert-butoxide) was added again under the air. A lid of the ball mill jar was closed and the ball mill jar was attached to a ball mill (Model MM400, manufactured by Retsch Co., Ltd.), followed by shaking and stirring (30 Hz) for 99 minutes. After completion of the reaction, the reaction mixture was passed through short silica gel column chromatography with ethyl acetate to remove the catalyst and the inorganic salt. After removing the ethyl acetate by an evaporator, the objective cross-coupling product was isolated by purification using silica gel column chromatography (175.5 mg, 0.475 mmol, isolated yield of 95%).

The result of Example 1 is also shown in Table 1.

The reaction of Example 1 was observed by powder X-ray diffraction (PXRD). FIG. 1 shows the observation of the solid phase palladium-catalyzed C—N coupling reaction of Example 1 by the powder X-ray diffraction. At the start of the reaction (0 minute), only peaks of the 1-bromopyrene (1a) and the diphenylamine (2-1a) as starting materials were observed. Since the 1,5-cyclooctadiene (4a) is liquid, no peak is observed in the PXRD. Twenty minutes (20 minutes) after the start of the reaction, the peaks of the 1-bromopyrene (1a) and the diphenylamine (2-1a) as the starting materials exist, but new peaks attributed to the cross-coupling product (3-1a) produced by the reaction of the starting materials and NaBr were observed. Sixty minutes (60 minutes) after the start of the reaction, the peaks attributed to the starting materials disappeared completely in the PXRD, and only the peaks attributed to the cross-coupling product (3-1a) and the NaBr were observed. This means that the reaction selectively proceeds while the starting materials remains in a solid state without the starting materials being dissolved in the 1,5-cyclooctadiene during the reaction and without the starting materials being liquefied.

Examples 2 to 6 and Comparative Example 1

Using the same method as in Example 1, except that the 1,5-cyclooctadiene (4a) in Example 1 was replaced by each of cyclooctene (4b), cyclohexene (4c), 4-octyne (4d), 1-hexene (4e) and 3-hexene (4f), reactions of Examples 2 to 6 were performed to obtain cross-coupling reaction products in which a C—N bond is formed. Using the same method as in Example 1, except that the 1,5-cyclooctadiene (4a) in Example 1 was not used, a reaction of Comparative Example 1 was performed to obtain a cross-coupling reaction product in which a C—N bond is formed. Results of Examples 2 to 6 and Comparative Example 1 are shown in Table 1.

TABLE 1

| Example | 1 | 2 | 3 | 4 | 5 | 6 | Comparative Example 1 |
|---|---|---|---|---|---|---|---|
| Compound (4) | 4a | 4b | 4c | n-Pr—≡—n-Pr 4d | 4e | 4f | — |
| Yield(%) | 99% | 96% | 92% | 66% | 98% | 89% | 28% |

In the reactions of Examples 1 to 6, by adding the compound (4) having a C—C double or triple bond, the yields of all the cross-coupling reactions were significantly improved, and the reaction proceeded sufficiently without using a solvent. Meanwhile, in the reaction of Comparative Example 1 in which the compound (4) was not used, the yield was 28% and the cross-coupling reaction did not proceed sufficiently.

Examples 7 to 10

Using the same method as in Example 1, except that the diphenylamine (2-1a) in Example 1 was replaced by amino compounds (2-1b to 2-1e) shown in Table 2, reactions of Examples 7 to 10 were performed to obtain cross-coupling reaction products. The results of Examples 7 to 10 are shown in Table 2.

TABLE 2

| | | | | |
|---|---|---|---|---|
| Example | 7 | 8 | 9 | 10 |
| Compound (2) | 2-1b | 2-1c | 2-1d | 2-1e |
| Compound (3) | 3-1b | 3-1c | 3-1d | 3-1e |
| Yield(%) | 88% | 68% | 72% | 81% |

In the reactions of Examples 7 to 10, by adding the compound (4) having a C—C double or triple bond, cross-coupling products were obtained in good yield without using a solvent.

Examples 11 to 30

Using the same manner as in Example 1, except that the 1-bromopyrene (1a) in Example 1 was replaced by each of compounds (1b to 1u) mentioned in Tables 3 to 4, reactions of Examples 11 to 30 were performed to obtain cross-coupling reaction products in which a C—N bond is formed. The results of Examples 11 to 30 are shown in Tables 3 to 4.

TABLE 3
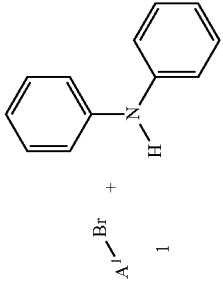
| Example | 11 | 12 | 13 | 14 | 15 |
|---|---|---|---|---|---|
| Compound (1) |  1b |  1c |  1d |  1e |  1f |
| Compound (3) |  3-1f |  3-1g | 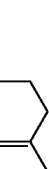 3-1h | 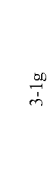 3-1i | 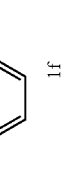 3-1j |
| Yield(%) | 94% | 70% | 90% | 80% | 71% |

TABLE 3-continued $$\text{A}^1\text{—Br} + \underset{\text{2-1a}}{\text{Ph}_2\text{NH}} \xrightarrow[\substack{\text{cyclooctadiene (0.2 micro L/mg)} \\ \text{ball mil (99 min, 30 Hz)}}]{\substack{5 \text{ mol \% Pd(OAc)}_2 \\ 5 \text{ mol \% t-Bu}_3\text{P} \\ \text{Na(O-t-Bu) (1.5 equiv)}}} \text{A}^1\text{—NPh}_2 \quad 3\text{-}1$$

| Example | 16 | 17 | 18 | 19 | 20 |
|---|---|---|---|---|---|
| Compound (1) | 1g | 1h | 1i | 1j | 1k |
| Compound (3) | 3-1k | 3-1l | 3-1m | 3-1n | 3-1o |
| Yield(%) | 55% | 96% | 89% | 80% | 75% |

TABLE 4

| Example | 21 | 22 | 23 | 24 | 25 |
|---|---|---|---|---|---|
| Compound (1) | 1l | 1m | 1n | 1o | 1p |
| Compound (3) | 3-1p | 3-1q | 3-1r | 3-1s | 3-1t |
| Yield(%) | 99% | 85% | 90% | 95% | 92% |

TABLE 4-continued $A^1-Br + \underset{H}{Ph-N-Ph} \xrightarrow[\text{ball mill (99 min, 30 Hz)}]{\substack{5\text{ mol }\%\text{ Pd(OAc)}_2 \\ 5\text{ mol }\%\text{ t-Bu}_3\text{P} \\ \text{Na(O-t-Bu) (1.5 equiv)} \\ \text{cod (0.2 micro L/mg)}}} A^1-N(Ph)_2$ 1    2-1a    3-1

| Example | 26 | 27 | 28 | 29 | 30 |
|---|---|---|---|---|---|
| Compound (1) | 1q | 1r | 1s | 1t | 1u |
| Compound (3) | 3-1u | 3-1v | 3-1w | 3-1x | 3-1y |
| Yield(%) | 67% | 62% | 82% | 57% | 55% |

In the reactions of Examples 11 to 30, by adding the compound (4) having a C—C double or triple bond, cross-coupling products were obtained in good yield without using a solvent.

Examples 31 to 32

Using the same manner as in Example 1, except that the 1-bromopyrene (1a) in Example 1 was replaced by each of compounds (1v to 1w) mentioned in Table 5, and the diphenylamine (2-1a) in Example 1 was replaced by bis-(4-methoxyphenyl)amine (2-1c), reactions of Examples 31 to 32 were performed to obtain cross-coupling reaction products in which a C—N bond is formed. The results of Examples 31 to 32 are shown in Table 5.

TABLE 5

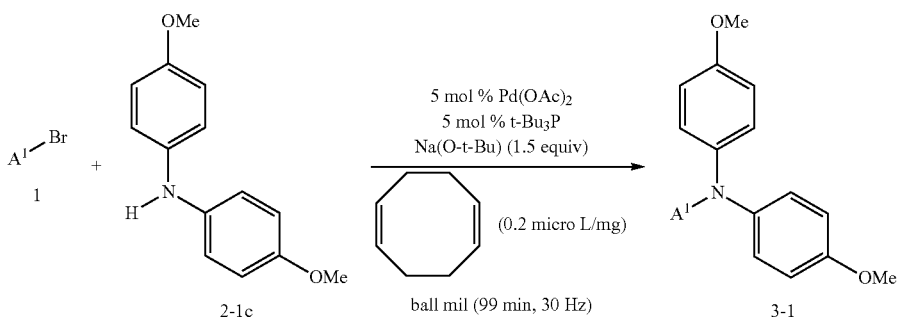

| Example | 31 | 32 |
|---|---|---|

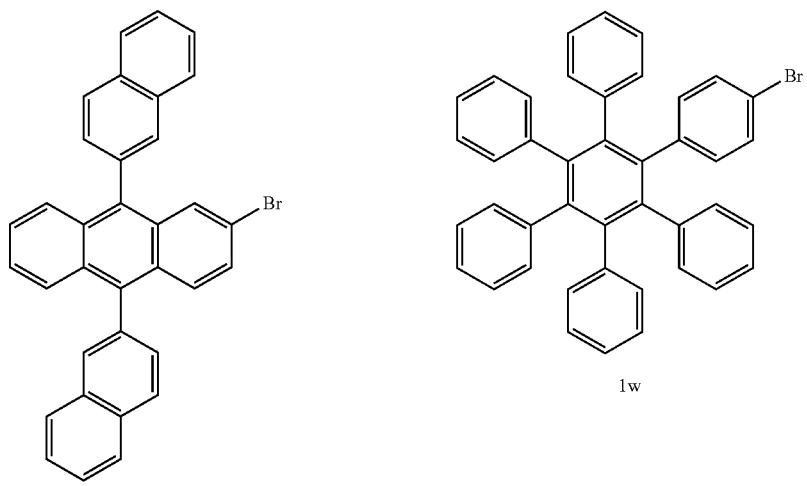

Compound (1): 1v, 1w

TABLE 5-continued

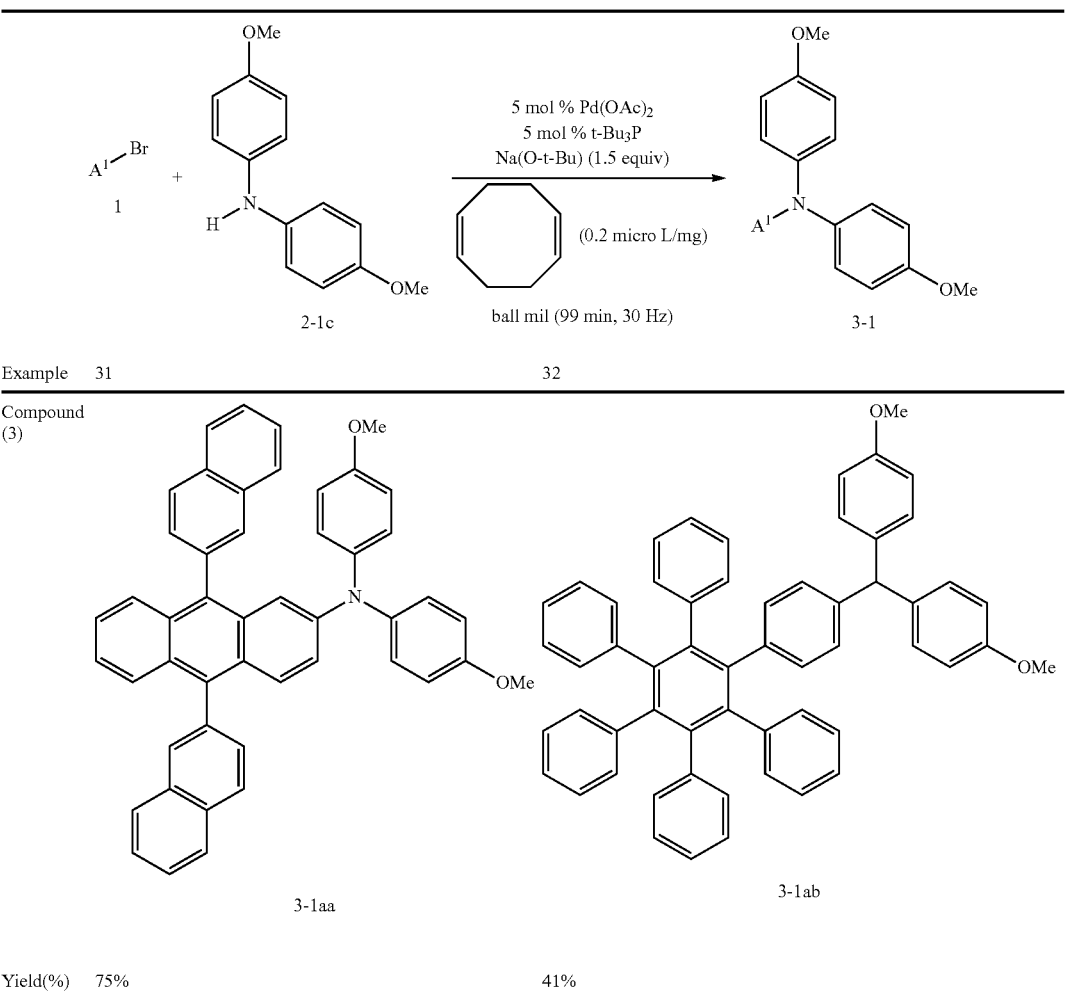

| Example | 31 | 32 |
|---|---|---|
| Compound (3) | 3-1aa | 3-1ab |
| Yield(%) | 75% | 41% |

In the reactions of Examples 31 to 32, by adding the compound (4) having a C—C double or triple bond, cross-coupling products were obtained in good yield without using a solvent.

Examples 33 to 34

Using the same manner as in Example 1, except that the 1-bromopyrene (1a) in Example 1 was replaced by each of dibromo compounds (1x to 1y) having two leaving groups mentioned in Table 6, and the diphenylamine (2-1a) was replaced by bis-(4-methoxyphenyl)amine (2-1c) for Example 34, reactions of Examples 33 to 34 were performed to obtain cross-coupling reaction products in which two C—N bonds are formed. Since the compounds (1x to 1y) have two leaving groups, the compound (2), the sodium tert-butoxide, the palladium acetate and the tri-tert-butylphosphine were used twice as many mols as the reaction of Example 1 to maintain the equivalence relationship of the cross-coupling reaction. The results of Examples 33 to 34 are shown in Table 6.

TABLE 6

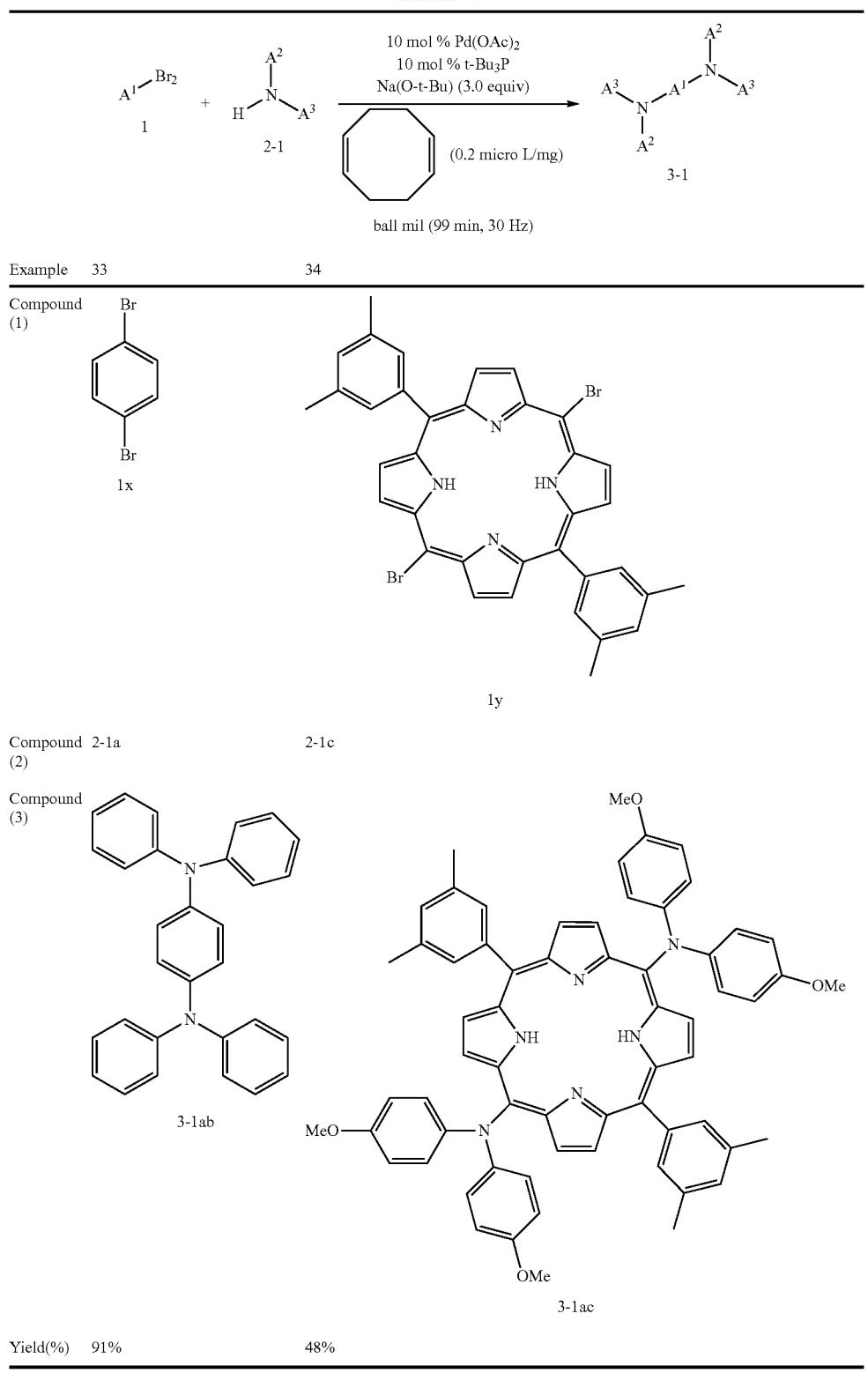

In the reactions of Examples 33 to 34, by adding the compound (4) having a C—C double or triple bond, cross-coupling reaction products were obtained in good yield without using a solvent, with respect to the compounds (1x to 1y) having two leaving groups.

Example 35

Using the same method as in Example 1, except that the 1-bromopyrene (1a) in Example 1 was replaced by tetra-bromo compound (1z) having four leaving groups mentioned in Table 7, the diphenylamine (2-1a) was replaced by bis-(4-methoxyphenyl)amine (2-1c), 15 mol % of the palladium acetate and 15 mol % of the tri-t-butylphosphine were used, and 5.0 equivalents of (2-1c) was used, a reaction of Example 35 was performed to obtain a cross-coupling reaction product in which four C—N bonds are formed. The result of Example 35 is shown in Table 7.

Example 36

Using the same method as in Example 1, except that the 1-bromopyrene (1a) in Example 1 was replaced by 2-chloronaphthalene (1aa), a reaction of Example 36 was performed to obtain a cross-coupling reaction product (3-1h) in

TABLE 7

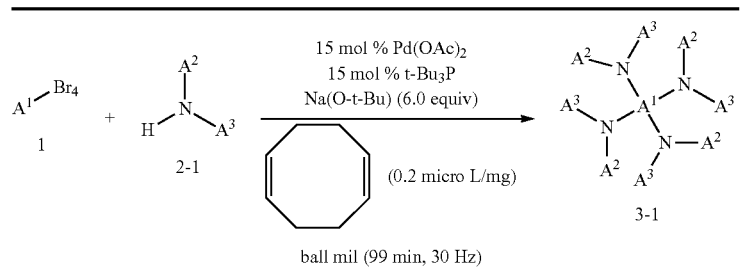

ball mil (99 min, 30 Hz)

| Example | 35 |
|---|---|
| Compound (1) | 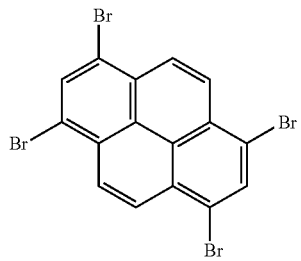  1z |
| Compound (2) | Compound 2-1c |
| Compound (3) | 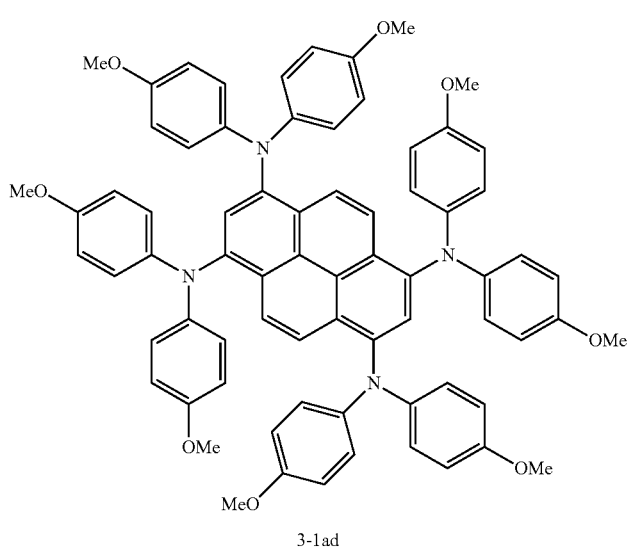 [SMILES: COc1ccc(N(c2ccc(OC)cc2)c2cc(N(c3ccc(OC)cc3)c3ccc(OC)cc3)c3ccc4c(N(c5ccc(OC)cc5)c5ccc(OC)cc5)cc(N(c5ccc(OC)cc5)c5ccc(OC)cc5)c5ccc2c3c54)cc1]  3-1ad |
| Yield(%) | 89% |

In the reaction of Example 35, by adding the compound (4) having a C—C double or triple bond, a cross-coupling reaction product was obtained in good yield without using a solvent, with respect to the compound (1z) having four leaving groups.

which a C—N bond is formed, which is the same as the reaction product of Example 13.

The yield of Example 36 was 73% and slightly decreased as compared with the yield of Example 13, but the compound (3-1h) was obtained in good yield. The decrease in yield is considered to be due to the replacement of bromine as a leaving group by chlorine.

Example 37

Using the same method as in Example 1, except that the diphenylamine (2-1a) of Example 1 was replaced by di(4-methoxyphenyl)amine (2-1b), and both the palladium acetate and the tri-t-butylphosphine were used in an amount of 2 mol %, a reaction of Example 37 was performed to obtain a cross-coupling reaction product (3-1b) in which a C—N bond is formed, which is the same as the reaction product of Example 7.

The yield of Example 37 was 92%, which was about the same as the yield of Example 7, and the compound (3-1b) was obtained in good yield. This means that reducing the amount of the catalyst does not exert a significant effect.

Example 41

In a 1.5 mL stainless steel ball mill jar containing three stainless steel balls having a diameter of 3 mm, 4-bromobiphenyl (1i) (117.1 mg, 0.5 mmol, 1.0 equiv), bis(pinacolato)diboron (2-2a) (144.6 mg, 0.55 mmol, 1.1 equiv) and palladium acetate (3.4 mg, 0.015 mmol, 3 mol %) were charged under the air. The ball mill jar was transferred to a glove box, and then tri-tert-butylphosphine (3.5 mg, 0.015 mmol, 3 mol %) and potassium hydroxide (84.2 mg, 1.5 mmol, 3.0 equiv) were added under argon atmosphere. The ball mill jar was removed from the glove box, and then 1,7-octadiene (4 g) (42 microL, 0.12 microL/mg based on the total mass of the 4-bromobiphenyl, the bis(pinacolato) diboron, the palladium acetate, the tri-tert-butylphosphine and the potassium hydroxide) and water (30 microL, 3.3 equiv) were added again under the air. A lid of the ball mill jar was closed and the ball mill jar was attached to a ball mill (Model MM400, manufactured by Retsch Co., Ltd.), followed by shaking and stirring (25 Hz) for 99 minutes. After completion of the reaction, the reaction mixture was passed through short silica gel column chromatography with ethyl acetate to remove the catalyst and the inorganic salt. After removing the ethyl acetate by an evaporator, the objective cross-coupling product (3-2a) was isolated by purification using silica gel column chromatography (94.8 mg, 0.335 mmol, isolated yield of 67%, NMR yield of 83%).

Examples 42 to 44

Using the same method as in Example 41, except that the 4-bromobiphenyl (1i) in Example 41 was replaced by each of compounds (1n, 1d, 1k) mentioned in Table 8, reactions of Examples 42 to 44 were performed to obtain cross-coupling reaction products (3-2b, 3-2c, 3-2d) in which a C—B bond is formed. The results of Examples 42 to 44 are shown in Table 8.

TABLE 8

| Example | 41 | 42 | 43 | 44 |
|---|---|---|---|---|
| Compound (1) | 1i | 1n | 1d | 1k |
| Compound (3) | 3-2a | 3-2b | 3-2c | 3-2d |
| Yield(%) | 67% | 60% | 68% NMRyield | 54% |

In the reactions of Examples 42 to 44, by adding the compound (4) having a C—C double or triple bond, cross-coupling reaction products in which a C—B bond is formed were obtained in good yield without using a solvent. (3-2c) indicated an NMR yield and others indicted isolated yields. Water is used as an additional accelerator.

Example 51

In a 1.5 mL stainless steel ball mill jar containing stainless steel balls having a diameter of 5 mm, 4-bromobiphenyl (1i) (69.9 mg, 0.3 mmol, 1.0 equiv), [4-(dimethylamino)phenyl]

boronic acid (2-3a) (59.4 mg, 0.36 mmol, 1.2 equiv), palladium acetate (2.0 mg, 0.009 mmol, 3 mol %), DavePhos (2-dicyclohexylphosphino-2'-(N,N-dimethylamino)biphenyl) (5.3 mg, 0.0135 mmol, 3 mol %), cesium fluoride (136.7 mg, 0.9 mmol, 3.0 equiv), 1,5-cyclooctadiene (4a) (33 microL, 0.12 microL/mg based on the total mass of the 4-bromobiphenyl, the [4-(dimethylamino)phenyl]boronic acid, the cesium fluoride, the palladium acetate and the DavePhos) and water (20 microL, 3.7 equiv) were charged under the air. A lid of the ball mill jar was closed and the ball mill jar was attached to a ball mill (Model MM400, manufactured by Retsch Co., Ltd.), followed by shaking and stirring (25 Hz) for 99 minutes. After completion of the reaction, the reaction mixture was passed through short silica gel column chromatography with ethyl acetate/chloroform (1:1, v:v) to remove the catalyst and the inorganic salt. After removing the solvent by an evaporator, the objective cross-coupling product was isolated by purification using silica gel column chromatography (74.6 mg, 0.273 mmol, isolated yield of 91%, NMR yield of 97%).

Examples 52 to 60

Using the same method as in Example 51, except that the [4-(dimethylamino)phenyl]boronic acid (2-3a) in Example 51 was replaced by each of compounds (2-3b to 2-3j) mentioned in Table 9, reactions of Examples 52 to 60 were performed to obtain cross-coupling reaction products (3-3b to 3-3j) in which a C—C bond is formed. The results of Examples 52 to 60 are shown in Table 9.

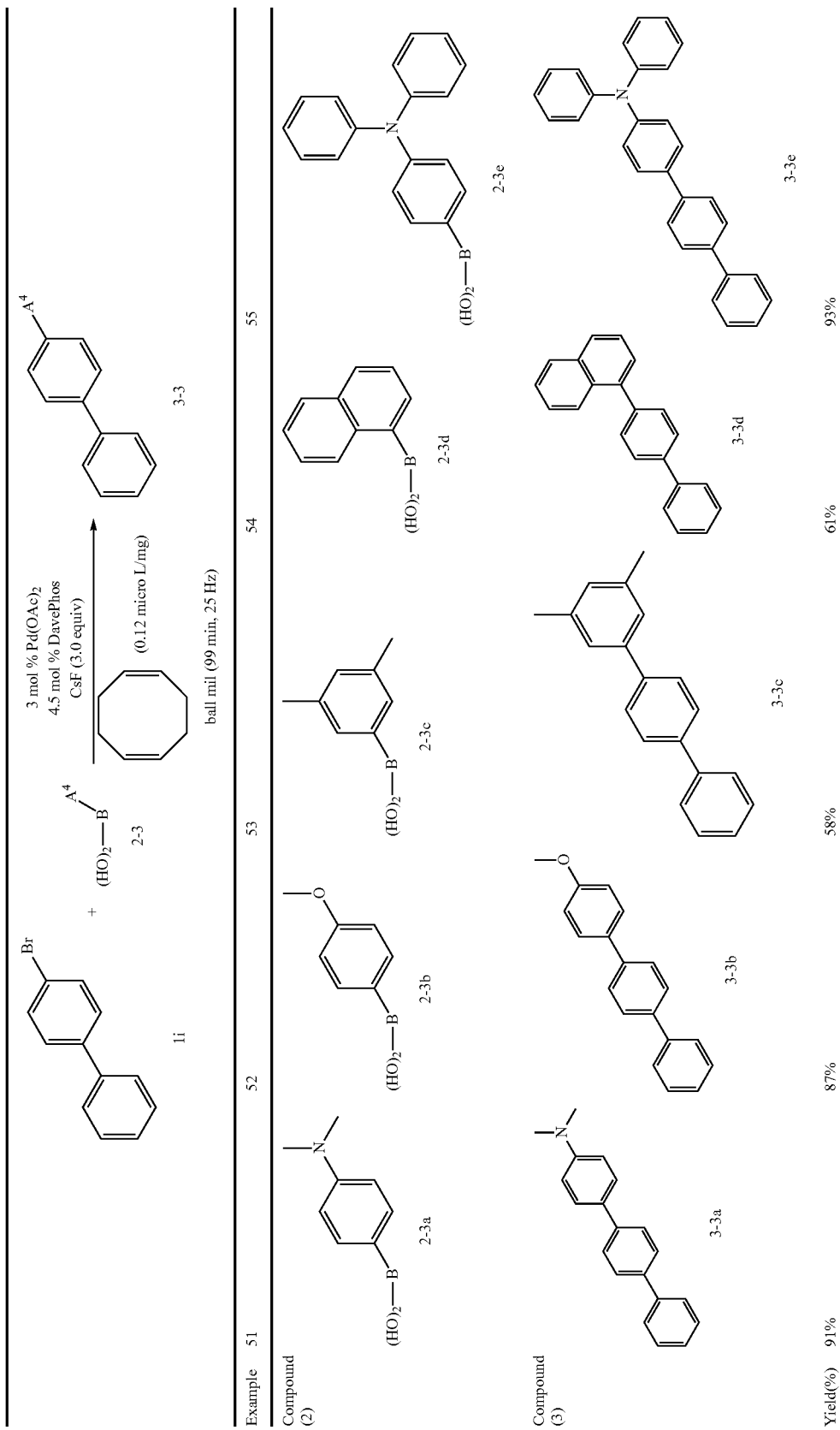

TABLE 9-continued

| Example | 56 | 57 | 58 | 59 | 60 |
|---|---|---|---|---|---|
| Compound (2) | 2-3f | 2-3g | 2-3h | 2-3i | 2-3j |
| Compound (3) | 3-3f | 3-3g | 3-3h | 3-3i | 3-3j |
| Yield(%) | 91% | 99% | 83% | 99% | 87% |

In the reactions of Examples 52 to 60, by adding the compound (4) having a C—C double or triple bond, cross-coupling reaction products in which a C—C-bond is formed were obtained in good yield without using a solvent. The yield in Table 9 indicates an isolated yield. Water is used as an additional accelerator.

Example 61

In a 1.5 mL stainless steel ball mill jar containing stainless steel balls having a diameter of 5 mm, 4-bromobenzene (1aa) (0.3 mmol, 1.0 equiv), benzyl alcohol (2-4a) (0.45 mmol, 1.5 equiv) and palladium acetate (0.015 mmol, 5 mol %) were charged under the air. The ball mill jar was transferred to a glove box, and then tBuBrettPhos (2-(di-tert-butylphosphino)-2',4',6'-triisopropyl-3,6-dimethoxy-1, 1'-biphenyl) (0.015 mmol, 5 mol %) and sodium tert-butoxide (0.36 mmol, 1.2 equiv) were added under argon atmosphere. A lid of the ball mill jar was closed and the ball mill jar was attached to a ball mill (Model MM400, manufactured by Retsch Co., Ltd.), followed by shaking and stirring (30 Hz) for 60 minutes. After completion of the reaction, the reaction mixture was passed through short silica gel column chromatography with ethyl acetate/chloroform (1:1, v:v) to remove the catalyst and the inorganic salt. After removing the solvent by an evaporator, the objective cross-coupling product was obtained by purification using silica gel column chromatography (NMR yield of 45%).

The result of Example 61 is shown in Table 10.

TABLE 10

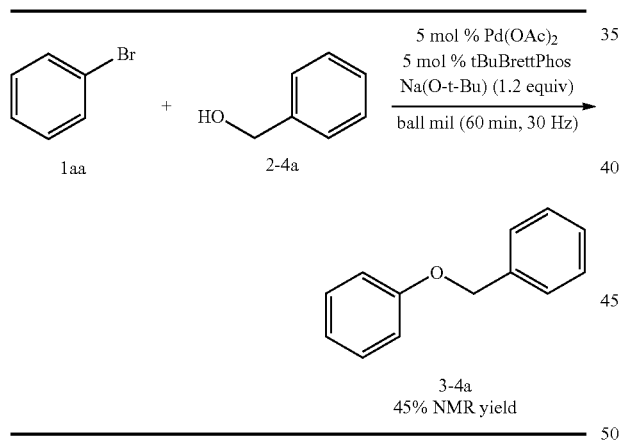

INDUSTRIAL APPLICABILITY

The cross-coupling reaction method of the embodiment of the present invention is capable of proceeding efficiently to form a chemical bond selected from C—N, C—B, C—C, C—O and C—S bonds, while reducing an amount of an organic solvent used, preferably without substantially using an organic solvent, preferably under milder reaction conditions in a shorter time, in higher yield.

Therefore, by using the cross-coupling reaction method of the embodiment of the present invention, it is possible to efficiently produce a cross-coupling product in which a chemical bond selected from C—N, C—B, C—C, C—O and C—S bonds is formed, while reducing an amount of an organic solvent used, preferably without substantially using an organic solvent, preferably under milder reaction conditions in a shorter time, in higher yield.

RELATED APPLICATIONS

This application claims priority under Article 4 of the Paris Convention or Article 41 of the Japanese Patent Law on Japanese Patent Application No. 2018-198915 filed on Oct. 23, 2018 in Japan, the disclosure of which is incorporated by reference herein.

The invention claimed is:
1. A cross-coupling reaction method which forms a chemical bond selected from C—N, C—B, C—C, C—O and C—S bonds, the method comprising:
 preparing an aromatic compound (1) having a leaving group;
 preparing a compound (2) capable of undergoing a cross-coupling reaction selected from an aromatic amino compound (2-1), a diboronic acid ester or the like (2-2), an aromatic boronic acid or the like (2-3), an aromatic compound (2-4) having a hydroxyl group and an aromatic compound (2-5) having a thiol group, wherein the aromatic amino compound (2-1) has an amino group bonded to an aromatic group, and the amino group has hydrogen; and
 mixing the compound (1) with the compound (2) and performing a cross-coupling reaction of the compound (1) with the compound (2) in the presence of a palladium catalyst, a base and a compound (4) having a carbon-carbon double bond or a carbon-carbon triple bond (excluding aromatic), in the absence of a solvent.
2. The cross-coupling reaction method according to claim 1, wherein the aromatic compound (1) having a leaving group is represented by the following general formula (I):

$A^1$-Xn wherein $A^1$ is selected from an optionally substituted aryl group and an optionally substituted heteroaryl group, X is a leaving group, and n is an integer of 1 or more;
 the aromatic amino compound (2-1) is represented by the following general formula (II-1):

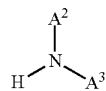

II-1 wherein $A^2$ and $A^3$ are each independently selected from hydrogen, an optionally substituted aryl group and an optionally substituted heteroaryl group, $A^2$ and $A^3$ are not simultaneously hydrogen, and $A^2$ and $A^3$ may be bonded to each other;
 the diboronic acid ester or the like (2-2) is represented by the following general formula (II-2):

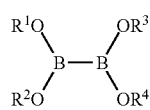

II-2 wherein $R^1$ to $R^4$ are each independently selected from hydrogen, an optionally substituted alkyl group and an optionally substituted aryl group, $R^1$ and $R^2$ may be bonded to each other, and $R^3$ and $R^4$ may be bonded to each other;

the aromatic boronic acid or the like (2-3) is represented by the following general formula (II-3):

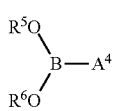

wherein $R^5$ to $R^6$ are each independently selected from hydrogen, an optionally substituted alkyl group and an optionally substituted aryl group, $R^5$ and $R^6$ may be bonded to each other, and $A^4$ is selected from an optionally substituted aryl group and an optionally substituted heteroaryl group;

the aromatic compound (2-4) having a hydroxyl group is represented by the following general formula (II-4):

wherein $A^5$ is selected from an optionally substituted aryl group and an optionally substituted heteroaryl group, and m is an integer of 0 to 20; and the aromatic compound (2-5) having a thiol group is represented by the following general formula (II-5):

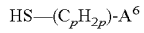

wherein $A^6$ is selected from an optionally substituted aryl group and an optionally substituted heteroaryl group, and p is an integer of 0 to 20.

3. The method according to claim 1, wherein the aromatic compound (1) having a leaving group comprises, as the leaving group, one selected from chloro, bromo, iodo, a diazonium salt, trifluoromethanesulfonate and a carboxylic acid derivative, and comprises, as an aromatic group, one selected from an optionally substituted aryl group and an optionally substituted heteroaryl group, the optionally substituted aryl group comprises phenyl group, naphthyl group, anthracenyl group, phenanthrenyl group, biphenyl group, terphenyl group, pyrenyl group, perylenyl group and triphenylenyl group, the optionally substituted heteroaryl group comprises a sulfur-containing heteroaryl group; an oxygen-containing heteroaryl group; a nitrogen-containing heteroaryl group; and a heteroaryl group containing two or more heteroatoms, the aromatic amino compound (2-1) can comprise up to two aromatic groups, and the aromatic group can be selected from an optionally substituted aryl group and an optionally substituted heteroaryl group, the optionally substituted aryl group comprises phenyl group, naphthyl group, anthracenyl group, phenanthrenyl group, biphenyl group, terphenyl group, pyrenyl group, perylenyl group and triphenylenyl group, the optionally substituted heteroaryl group comprises a sulfur-containing heteroaryl group; an oxygen-containing heteroaryl group; a nitrogen-containing heteroaryl group; and a heteroaryl group containing two or more heteroatoms, the diboronic acid ester or the like (2-2) comprises a diboronic acid alkyl ester, a diboronic acid alkylene glycol ester, a diboronic acid aryl ester, a diboronic acid arylene glycol ester and tetrahydroxydiborane, the aromatic boronic acid or the like (2-3) comprises an aromatic boronic acid and an aromatic boronic acid ester, and comprises, as an aromatic group, one selected from an optionally substituted aryl group and an optionally substituted heteroaryl group, the optionally substituted aryl group comprises phenyl group, naphthyl group, anthracenyl group, phenanthrenyl group, biphenyl group, terphenyl group, pyrenyl group, perylenyl group and triphenylenyl group, the optionally substituted heteroaryl group comprises a sulfur-containing heteroaryl group; an oxygen-containing heteroaryl group; a nitrogen-containing heteroaryl group; and a heteroaryl group containing two or more heteroatoms, the aromatic compound (2-4) having a hydroxyl group comprises, as an aromatic group, one selected from an optionally substituted aryl group and an optionally substituted heteroaryl group, the optionally substituted aryl group comprises phenyl group, naphthyl group, anthracenyl group, phenanthrenyl group, biphenyl group, terphenyl group, pyrenyl group, perylenyl group and triphenylenyl group, the optionally substituted heteroaryl group comprises a sulfur-containing heteroaryl group; an oxygen-containing heteroaryl group; a nitrogen-containing heteroaryl group; and a heteroaryl group containing two or more heteroatoms, the aromatic compound (2-5) having a thiol group comprises, as an aromatic group, one selected from an optionally substituted aryl group and an optionally substituted heteroaryl group, the optionally substituted aryl group comprises phenyl group, naphthyl group, anthracenyl group, phenanthrenyl group, biphenyl group, terphenyl group, pyrenyl group, perylenyl group and triphenylenyl group, and the optionally substituted heteroaryl group comprises a sulfur-containing heteroaryl group; an oxygen-containing heteroaryl group; a nitrogen-containing heteroaryl group; and a heteroaryl group containing two or more heteroatoms.

4. The method according to claim 1, wherein the compound (4) having a carbon-carbon double bond or a carbon-carbon triple bond comprises a compound having at least one carbon-carbon double bond or at least one carbon-carbon triple bond, which may be either chain or cyclic, but comprises no aromatic.

5. The method according to claim 1, wherein a phosphine compound is allowed to coexist with the palladium catalyst.

6. The method according to claim 1, wherein the base comprises at least one selected from an inorganic base, an alkali metal alkoxide and an organic base.

7. The method according to claim 1, wherein equivalent ratio of the compound (1) to the compound (2) (compound (1)/compound (2)) is 10/1 to 1/10.

8. The method according to claim 1, wherein the palladium catalyst is allowed to exist in an amount of 0.5 mol % or more and 10 mol % or less based on number of mols (100%) obtained by multiplying number of mols of the compound (1) by valence of the compound (1).

9. The method according to claim 1, wherein the compound (4) is allowed to exist in an amount of 0.01 to 3 microL/mg based on the total mass of the compound (1), the compound (2), the palladium catalyst, the base and, if necessary, the phosphine compound.

10. The method according to claim 1, wherein the reaction is performed in the presence of the base in an amount of 0.5 equivalent or more and 10 equivalents or less per 1 equivalent of the compound (1).

11. A method for producing a cross-coupling reaction product, which comprises using the cross-coupling reaction method according to claim 1.

12. The method according to claim 1, wherein the method for mixing the compound (1) with the compound (2) and performing a cross-coupling reaction of the compound (1) with the compound (2) is selected from shaking, rubbing, pressing, dispersing, kneading and crushing.

* * * * *